(12) United States Patent
Radu et al.

(10) Patent No.: US 8,362,463 B2
(45) Date of Patent: Jan. 29, 2013

(54) ORGANOMETALLIC COMPLEXES

(75) Inventors: Nora Sabrina Radu, Landenberg, PA (US); Norman Herron, Newark, DE (US); Jeffrey Merlo, Wilmington, DE (US); Ying Wang, Wilmington, DE (US); Mark A. Guidry, New Castle, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1116 days.

(21) Appl. No.: 11/721,746

(22) PCT Filed: Dec. 28, 2005

(86) PCT No.: PCT/US2005/047476
§ 371 (c)(1),
(2), (4) Date: Aug. 22, 2008

(87) PCT Pub. No.: WO2006/072002
PCT Pub. Date: Jul. 6, 2006

(65) Prior Publication Data
US 2009/0206327 A1    Aug. 20, 2009

Related U.S. Application Data

(60) Provisional application No. 60/640,326, filed on Dec. 30, 2004, provisional application No. 60/694,914, filed on Jun. 28, 2005.

(51) Int. Cl.
*H01L 29/08* (2006.01)
*H01B 1/00* (2006.01)
*C07D 215/30* (2006.01)
*H01J 1/62* (2006.01)

(52) U.S. Cl. .......... 257/40; 252/500; 428/690; 313/504; 546/7

(58) Field of Classification Search .............. None
See application file for complete search history.

(56) References Cited

U.S. PATENT DOCUMENTS

| | | | |
|---|---|---|---|
| 6,303,238 B1 | 10/2001 | Thompson et al. | |
| 6,875,523 B2 | 4/2005 | Grushin et al. | |
| 2001/0019782 A1 | 9/2001 | Igarashi et al. | |
| 2002/0136924 A1 | 9/2002 | Higashi et al. | |
| 2003/0022019 A1* | 1/2003 | Seo et al. ................ | 428/690 |
| 2003/0047736 A1* | 3/2003 | Hayashi et al. ............ | 257/79 |
| 2006/0263631 A1 | 11/2006 | Lee et al. | |

FOREIGN PATENT DOCUMENTS

| | | |
|---|---|---|
| EP | 0992564 | 4/2000 |
| EP | 1191612 A2 | 3/2002 |
| EP | 1191614 A2 | 3/2002 |
| JP | 11-040355 | 2/1999 |
| JP | 11-067449 * | 3/1999 |
| JP | 2001-520450 | 10/2001 |
| JP | 2003 026688 | 1/2003 |

(Continued)

OTHER PUBLICATIONS

Rawlins et al., A Tungsten Organometallic Complex as a Spectroscopic Probe of Acrylate Polymerization in the Films, Polymer Preprints, 647-648, (1996).*

(Continued)

*Primary Examiner* — Camie Thompson
(74) *Attorney, Agent, or Firm* — Woodcock Washburn LLP

(57) ABSTRACT

Organometallic complexes are provided having at least one charge transporting ligand, and methods for making the same, as well as devices and sub-assemblies including the same.

18 Claims, 1 Drawing Sheet

FOREIGN PATENT DOCUMENTS

| | | |
|---|---|---|
| JP | 2004 359671 | 12/2004 |
| JP | 2006-135315 | 5/2006 |
| WO | WO 99/20081 | 4/1999 |
| WO | WO 99/52992 | 10/1999 |
| WO | WO 01/04512 A1 | 6/2001 |
| WO | WO 02/02714 A2 | 1/2002 |
| WO | WO 02/15645 A1 | 2/2002 |
| WO | WO 2007/070655 | 6/2007 |

OTHER PUBLICATIONS

Gustafsson, G. et al., "Flexible Light-Emitting Diodes made from Soluble Conducting Polymer", *Nature*, 1992, 357, 477-479.

Campbell, I.H. et al., "Excitation Transfer Processes in a phosphor-doped poly (p-phenylene vinylene) Light-Emitting Diode" *Physical Review B*, 65, 085210-1-085210-8.

Bradley, et al., "Electrophosphoresence from a doped polymer light emitting diode", *Synthetic. Metals.*, 2001, 116(1-3), 379-383.

Wang et al., "Novel bis(8-hydroxyquinoline) Phenolato-aluminum complexes for organic light-emitting diodes", Synthetic Metals, 2002, 131(1-3), 1-5.

* cited by examiner

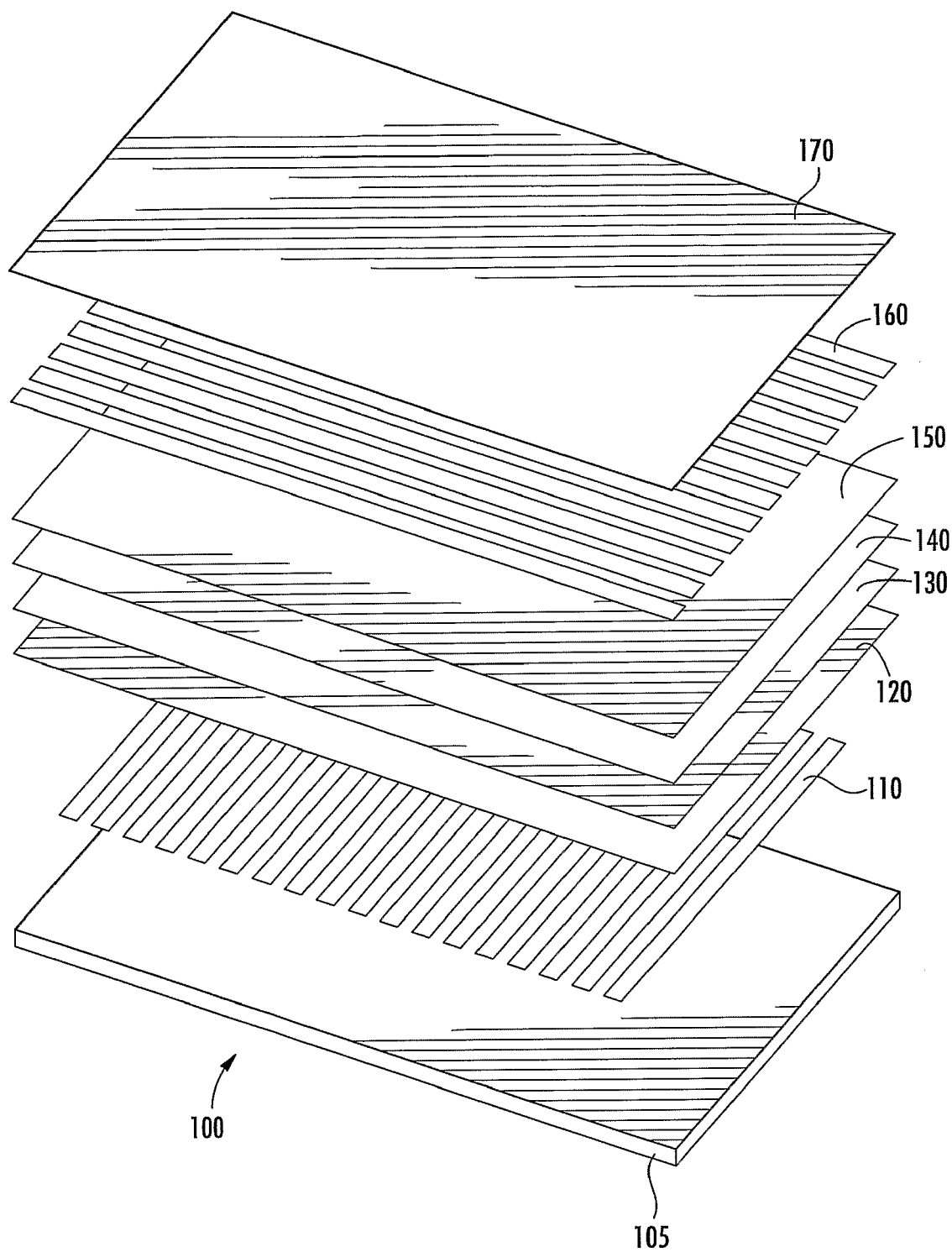

ORGANOMETALLIC COMPLEXES

CROSS-REFERENCE TO RELATED APPLICATIONS

This application is the National Stage of International Application No. PCT/US2005/047476, filed Dec. 28, 2005, which claims the benefit of U.S. Provisional Application Nos. 60/640,326, filed Dec. 30, 2004 and 60/694,914, filed Jun. 28, 2005, the disclosures of which are incorporated herein by reference in their entireties.

FIELD

This disclosure relates generally to organometallic complexes, for example, those found in organic electronic devices, and materials and methods for fabrication of the same.

BACKGROUND

Organic electronic devices convert electrical energy into radiation, detect signals through electronic processes, convert radiation into electrical energy, or include one or more organic semiconductor layers. An organic light-emitting diode (OLED) is an organic electronic device comprising an organic layer capable of electroluminescence. In some OLEDs, these photoactive organic layers comprise simple organic molecules, conjugated polymers, or organometallic complexes.

As can be appreciated, it is important to develop organometallic complexes.

SUMMARY

In one embodiment, an organometallic complex is provided having at least one charge transporting ligand, and methods for making the same, as well as devices and subassemblies including the same.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying FIGURE to improve understanding of concepts as presented herein.

FIG. 1 is a schematic diagram of an organic electronic device.

The FIGURE are provided by way of example and are not intended to limit the invention. Skilled artisans appreciate that objects in the FIGURE are illustrated for simplicity and clarity and have not necessarily been drawn to scale. For example, the dimensions of some of the objects in the FIGURE may be exaggerated relative to other objects to help to improve understanding of embodiments.

DETAILED DESCRIPTION

In one embodiment, there is provided a complex having the formula:

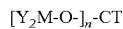

wherein:
M is a metal in a +2, +3, or +4 oxidation state;
Y is, independently at each occurrence, an hydroxyaryl-N-heterocycle, a bidentate Schiff base ligand, or both Y together form a tetradentate Schiff base ligand;
n is an integer from 1 to 4; and
CT is a charge transport group.

The term "hydroxyaryl-N-heterocycle" is intended to mean a ligand derived from a compound having at least one nitrogen-containing heterocyclic group and at least one aromatic group with a hydroxyl substituent, where the O of the hydroxyl group and the N of the heterocyclic ring can coordinate to a metal to form a 5- or 6-membered ring. The N-heterocyclic group and the hydroxy-substituted aromatic group can be joined with a single bond or fused together. The N-heterocyclic group and the hydroxy-substituted aromatic group can each comprise a single ring or two or more fused rings. The hydroxyaryl-N-heterocycle can be further substituted. Examples of substituents include, but are not limited to alkyl, fluoroalkyl, alkenyl, fluoroalkenyl, alkynyl, fluoroalkynyl, aryl, fluoroaryl, alkylaryl, alkoxy, aryloxy, fluoroalkoxy, fluoroaryloxy, heteroalkyl, fluoroheteroalkyl, heteroalkenyl, fluoroheteroalkenyl, heteroalkynyl, fluoroheteroalkynyl, heteroaryl, fluoroheteroaryl, heteroalkylaryl, heteroalkoxy, heteroaryloxy, fluoroheteroalkoxy, fluoroheteroaryloxy, cyano, dialkylamine, diarylamine, halide, a solvent-solubilizing group, and a Tg enhancing group.

The term "solvent-solubilizing" refers to a substituent that increases the solubility or dispersability of a material in at least one organic solvent, with respect to the material without the solvent-solubilizing substituent. In the case where the material is a ligand in a metal complex, the solvent-solubilizing substituent increases the solubility or dispersability of the uncomplexed, parent compound from which the ligand is derived. Examples of suitable solvent-solubilizing groups include, but are not limited to aryl groups having 6-20 carbons, heteroaryl groups having 4-20 carbons, alkyl groups having 1-10 carbons, and fluoroalkyl groups having 1-10 carbon atoms.

The term "Tg enhancing" refers to a substituent that raises the glass transition temperature of a material. In other words, the Tg of a compound having the Tg enhancing substituent, is greater that the Tg of the compound without the Tg enhancing substituent. In the case where the material is a ligand in a metal complex, the Tg enhancing substituent increases the Tg of the uncomplexed, parent compound from which the ligand is derived. Examples of suitable Tg enhancing groups include, but are not limited to aryl groups having 6-20 carbons, heteroaryl groups having 4-20 carbons, alkyl groups having 1-10 carbons.

In one embodiment, the N-heterocycle group is selected from the group consisting of pyridine, pyrimidine, quinoline, and isoquinoline. In one embodiment, the hydroxy-substituted aromatic group is phenol or naphthol.

In one embodiment, Y is 8-hydroxyquinolate or substituted 8-hydroxyquinolate. In one embodiment, 8-hydroxyquinolate is substituted in the 2 position. The term "8-hydroxyquinolate" refers to a ligand derived from the compound 8-hydroxyquinoline, wherein the hydrogen on the hydroxy group is removed and the oxygen is coordinated to a metal.

In one embodiment, Y is 2-(2-hydroxyaryl)pyridine, 2-(2-hydroxyaryl)quinoline, 1-(2-hydroxyaryl)isoquinoline, or 3-(2-hydroxyaryl)isoquinoline, which can be unsubstituted or substituted. In one embodiment, the 2-hydroxyaryl moiety is phenol.

The terms "2-(2-hydroxyaryl)pyridine," "2-(2-hydroxyaryl)quinoline," and "1-(2-hydroxyaryl)isoquinoline" when referring to a ligand, indicate the compound wherein the hydrogen on the hydroxy group is removed and the oxygen is coordinated to a metal.

In one embodiment, Y is a Schiff base ligand. In one embodiment the Schiff base ligand is a compound having Structure I:

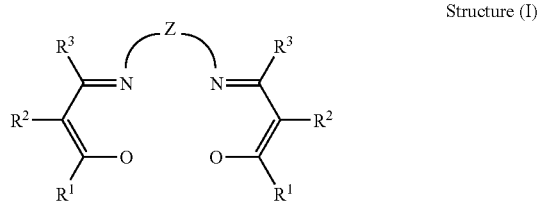

Structure (I)

wherein:

$R^1$, $R^2$, $R^3$ are independently hydrogen, deuterium, alkyl, heteroalkyl, aryl, or heteroaryl, or adjacent R groups can join together to form a 5- or 6-membered ring; and Z is alkylene, heteroalkylene, arylene, or heteroarylene.

In one embodiment, both Y together form a tetradentate Schiff base ligand having Structure II:

Structure (II)

wherein:

$R^1$, $R^2$, $R^3$, and $R^4$ are independently hydrogen, deuterium, alkyl, heteroalkyl, aryl, or heteroaryl, or adjacent R groups can join together to form a 5- or 6-membered ring.

In one embodiment of Structure I, both $R^1$ are the same and both $R^2$ are the same. In one embodiment, of Structure I or II, adjacent $R^1$ and $R^2$ join together to form a 6-membered aromatic ring. In one embodiment, the aromatic ring is substituted. Suitable substituents include, but are not limited to, alkyl, fluoroalkyl, alkenyl, fluoroalkenyl, alkynyl, fluoroalkynyl, aryl, fluoroaryl, alkylaryl, alkoxy, aryloxy, fluoroalkoxy, fluoroaryloxy, heteroalkyl, fluoroheteroalkyl, heteroalkenyl, fluoroheteroalkenyl, heteroalkynyl, fluoroheteroalkynyl, heteroaryl, fluoroheteroaryl, heteroalkylaryl, heteroalkoxy, heteroaryloxy, fluoroheteroalkoxy, fluoroheteroaryloxy, cyano, dialkylamine, diarylamine, halide, a solvent-solubilizing group, and a Tg enhancing group.

In one embodiment of Structure I, $R^3$ is hydrogen, deuterium, phenyl, or methyl.

In one embodiment, Z is, but is not limited to, alkylene having from 1-20 carbon atoms, phenylene, arylene having from 2 to 4 fused rings, bi-arylene, and aza-alkylene having from 2-20 carbon atoms. Such groups can be unsubstituted or substituted.

In one embodiment of Structure I, Z is alkylene having from 1-6 carbon atoms; 1,2-cyclohexylene; 1,2-phenylene; 4-methoxy-1,2-phenylene; 4,5-dimethyl-1,2-phenylene; o-binaphthalene-diyl; 3-aza-1,5-pentylene; 1,2-o-tolyl-1,2-ethylene; 1,2-dicyano-1,2-ethylene; or 2-p-t-butylbenzyl-1,3-propylene.

In one embodiment of Structure I, Z is ethylene, 1,2-cyclohexylene, or —$CH_2CH_2NHCH_2CH_2$—. The 1,2-cyclohexylene can be in either a cis or trans configuration.

In one embodiment of Structure II, $R^1$ and $R^2$ join together to form a 6-membered aromatic ring. In one embodiment, the aromatic ring is further substituted with alkyl, heteroalkyl, alkenyl, heteroalkenyl, alkynyl, heteroalkynyl, aryl, heteroaryl, alkoxy, aryloxy, or halide. In one embodiment, the aromatic ring is dichlorophenyl or alkylphenyl, where the alkyl has from 1 to 6 carbon atoms.

In one embodiment of Structure II, $R^4$ is alkyl having 1-20 carbon atoms or phenyl. In one embodiment, $R^4$ is substituted. Suitable substitutions include one or more halide or alkoxy.

In one embodiment, M is Al, Zn, Zr or Ga. In one embodiment, M is Al.

In one embodiment, CT is a hole transport group. In one embodiment CT is a triarylmethane group, a triarylamine group, or a carbazole group.

In one embodiment, CT is bis[4 (N,N-dimethylamino)-2-methylphenyl](phenyl)methane attached to oxygen at 4-phenyl.

In one embodiment, CT is 4'-(9-carbazolyl)-biphenyl attached to oxygen at the 4 position.

In one embodiment, CT is 4'-(1-naphthyl-phenylamino)-biphenyl attached to oxygen at the 4 position.

In one embodiment, CT is 4'-((4-N,N-diphenylamino-phenyl)-phenylamine)-biphenyl attached to oxygen at the 4 position.

In one embodiment, CT is 4'-(N,N'-(di-1-napthyl)-N'-phenylbenzidine)-N-biphenyl attached to oxygen at the 4 position.

In one embodiment, CT is 9-phenylcarbazole attached to oxygen at the 4 position.

In one embodiment, CT is 4'-(bis-(4-N,N-diphenylaminophenyl)-amine)-biphenyl attached to oxygen at the 4 position.

In one embodiment, CT is 9-phenylcarbazole attached to oxygen at the 2 position.

In one embodiment, CT is (4-(diphenylamino)phenyl)-phenylether attached to oxygen at the 4 position. In one embodiment, CT is (4-(N-carbazolyl)-1-phenyl)-phenylether attached to oxygen at the 4 position.

In one embodiment the CT group may be multivalent and n is greater than 1. The CT group is attached to multiple $MY_2$ centers via oxygen linkages.

In one embodiment n is 2. In one embodiment the CT group is [(N,N'-(diphenyl)(4-hydroxybiphenyl) benzidine attached via oxygen linkages at the 4-positions to two $MY_2$ centers.

In one embodiment, the CT group is 1,3-di(2-hydroxycarbazolyl)benzene attached via the oxygen linkages at the 2 positions of both carbazole rings to two $MY_2$ centers.

In one embodiment the CT group is 4,4'-(hexafluoroisopropylidine) diphenyl[(N,N'-(4-(N'',N''' diphenyl)aniline)(4-hydroxybiphenyl) attached via oxygen linkages at the 4-positions to two $MY_2$ centers.

In one embodiment, the CT group is 4,4'-(N-(4-hydroxycarbazolyl))-biphenyl attached via the oxygens at the 4 positions of the carbazole rings to two $MY_2$ centers.

In one embodiment, the CT group is [(3,6-di(N-(4-hydroxycarbazole)dibenzothiophene) attached via the oxygens at the 4 positions of the carbazole rings to two $MY_2$ centers.

In one embodiment, the CT group is 1,3-di(4-hydroxycarbazolyl)benzene attached via the oxygen linkages at the 4 positions of both carbazole rings to two $MY_2$ centers.

In one embodiment, CT is an electron transport group. In one embodiment, CT is an oxadiazole, a phenanthroline, or a quinoxaline, which may optionally be substituted.

In another embodiment, there is provided an electronic device comprising a photoactive layer and a cathode, and further comprising a complex having the formula:

$[Y_2M\text{-}O\text{-}]_n\text{-}CT$ wherein:
M is a metal in a +2, +3, or +4 oxidation state;
Y is, independently at each occurrence, an hydroxyaryl-N-heterocycle, a bidentate Schiff base ligand, or both Y together form a tetradentate Schiff base ligand;
n is an integer from 1 to 4: and
CT is a charge transport group,
wherein the complex is in the photoactive layer or a layer between the photoactive layer and the cathode.

In one embodiment, ligands for a metal are provided, the ligand having formula I, II, or III:

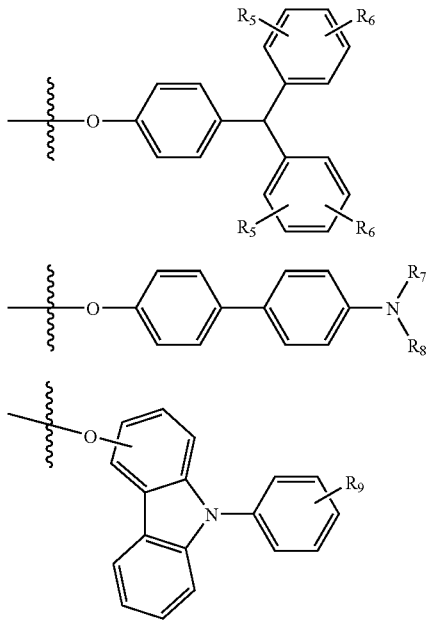

wherein:
$R_5$ is, independently, H or alkyl;
$R_6$ is $NR_7R_8$;
$R_7$ and $R_8$ are, independently, alkyl or aryl, or $R_7$ and $R_8$ cooperate to form aryl; and
$R_9$ is H or a bond to another ligand.

In one embodiment, the ligands have formula IV or V:

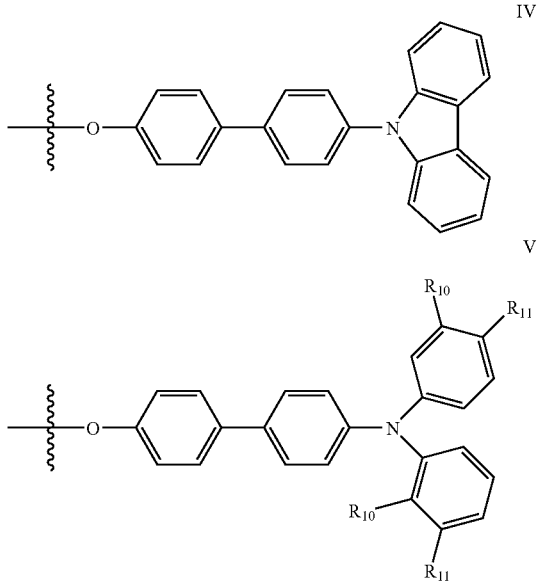

wherein:
$R_{10}$ and $R_{11}$ are, independently H, $NR_7R_8$, aryl, or a bond to another ligand, or $R_{10}$ and $R_{11}$ cooperate to form aryl.

In one embodiment, $R_5$ is alkyl at both occurrences and $NR_7R_8$ is $N(Me)_2$.

In one embodiment, $R_7$ and $R_8$ are each aryl.

In one embodiment, organometallic complexes are provided comprising formula:

$$[Y]_n MZ$$

wherein:
n is 1, 2, or 3;
M is a metal in a +2, +3, or +4 oxidation state;
Y is a ligand comprising 8-hydroxyquinoline or alkyl-substituted 8-hydroxyquinoline at each occurrence; and
Z is a ligand according to claim 1.

In one embodiment, M is Al, Zn, Zr, or Ga.

In one embodiment, the alkyl-substituted 8-hydroxyquinoline is substituted at the 2 position.

In one embodiment, the alkyl-substituted 8-hydroxyquinoline is 2-methyl-8-hydroxyquinoline.

In one embodiment, compositions are provided comprising the above-described compounds or complexes and at least one solvent, processing aid, charge transporting material, or charge blocking material. These compositions can be in any form, including, but not limited to solvents, emulsions, and colloidal dispersions. Device Referring to FIG. 1, an exemplary organic electronic device 100 is shown. The device 100 includes a substrate 105. The substrate 105 may be rigid or flexible, for example, glass, ceramic, metal, or plastic. When voltage is applied, emitted light is visible through the substrate 105.

A first electrical contact layer 110 is deposited on the substrate 105. For illustrative purposes, the layer 110 is an anode layer. Anode layers may be deposited as lines. The anode can be made of, for example, materials containing or comprising metal, mixed metals, alloy, metal oxides or mixed-metal oxide. The anode may comprise a conducting polymer, polymer blend or polymer mixtures. Suitable metals include the Group 11 metals, the metals in Groups 4, 5, and 6, and the Group 8, 10 transition metals. If the anode is to be light-transmitting, mixed-metal oxides of Groups 12, 13 and 14 metals, such as indium-tin-oxide, are generally used. The anode may also comprise an organic material, especially a conducting polymer such as polyaniline, including exemplary materials as described in *Flexible Light-Emitting Diodes Made From Soluble Conducting Polymer*, Nature 1992, 357, 477-479. At least one of the anode and cathode should be at least partially transparent to allow the generated light to be observed.

An optional buffer layer 120, and optionally other layers such as hole transport materials, may be deposited over the anode layer 110, the latter being sometimes referred to as the "hole-injecting contact layer." Examples of buffer materials and material suitable for optional hole transport materials suitable for use as the layer 120 or the optional additional layer have been summarized, for example, in Kirk Othmer, Encyclopedia of Chemical Technology, Vol. 18, 837-860 ($4^{th}$ ed. 1996). Both hole transporting "small" molecules as well as oligomers and polymers may be used. Hole transporting molecules include, but are not limited to: N,N' diphenyl-N,N'-bis(3-methylphenyl)-[1,1'-biphenyl]-4,4'-diamine (TPD), 1,1 bis[(di-4-tolylamino) phenyl]cyclohexane (TAPC), N,N' bis(4-methylphenyl)-N,N'-bis(4-ethylphenyl)-[1,1'-(3,3'-dimethyl)biphenyl]-4,4'-diamine (ETPD), tetrakis (3-methylphenyl)-N,N,N',N'-2,5-phenylenediamine (PDA), a-phenyl 4-N,N-diphenylaminostyrene (TPS), p (diethylamino)

benzaldehyde diphenylhydrazone (DEH), triphenylamine (TPA), bis[4 (N,N-diethylamino)-2-methylphenyl](4-methylphenyl)methane (MPMP), 1 phenyl-3-[p-(diethylamino)styryl]-5-[p-(diethylamino)phenyl] pyrazoline (PPR or DEASP), 1,2 trans-bis(9H-carbazol-9-yl)cyclobutane (DCZB), N,N,N',N' tetrakis(4-methylphenyl)-(1,1'-biphenyl)-4,4'-diamine (TTB), and porphyrinic compounds, such as copper phthalocyanine. Useful hole transporting polymers include, but are not limited to, polyvinylcarbazole, (phenylmethyl)polysilane, and polyaniline. Conducting polymers are useful as a class. It is also possible to obtain hole transporting polymers by doping hole transporting moieties, such as those mentioned above, into polymers such as polystyrenes and polycarbonates.

An organic layer 130 may be deposited over the buffer layer 120 when present, or over the first electrical contact layer 110. In some embodiments, the organic layer 130 may be a number of discrete layers comprising a variety of components. Depending upon the application of the device, the organic layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector).

Other layers in the device can be made of any materials which are known to be useful in such layers upon consideration of the function to be served by such layers.

Any organic electroluminescent ("EL") material can be used as a photoactive material (e.g., in layer 130). Such materials include, but are not limited to, fluorescent dyes, small molecule organic fluorescent compounds, fluorescent and phosphorescent metal complexes, conjugated polymers, and mixtures thereof. Examples of fluorescent dyes include, but are not limited to, pyrene, perylene, rubrene, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of Iridium with phenylpyridine, phenylquinoline, or phenylpyrimidine ligands as disclosed in Petrov et al., Published PCT Application WO 02/02714, and organometallic complexes described in, for example, published applications US 2001/0019782, EP 1191612, WO 02/15645, and EP 1191614; and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In one embodiment of the devices of the invention, photoactive material can be an organometallic complex. In another embodiment, the photoactive material is a cyclometalated complex of iridium or platinum. Other useful photoactive materials may be employed as well. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. Nos. 6,303,238, Bradley et al., in *Synth. Met.* 2001, 116 (1-3), 379-383, and Campbell et al., in Phys. Rev. B, Vol. 65 085210.

A second electrical contact layer 160 is deposited on the organic layer 130. For illustrative purposes, the layer 160 is a cathode layer.

Cathode layers may be deposited as lines or as a film. The cathode can be any metal or nonmetal having a lower work function than the anode. Exemplary materials for the cathode can include alkali metals, especially lithium, the Group 2 (alkaline earth) metals, the Group 12 metals, including the rare earth elements and lanthanides, and the actinides. Materials such as aluminum, indium, calcium, barium, samarium and magnesium, as well as combinations, can be used. Lithium-containing and other compounds, such as LiF and $Li_2O$, may also be deposited between an organic layer and the cathode layer to lower the operating voltage of the system.

An electron transport layer 140 or electron injection layer 150 is optionally disposed adjacent to the cathode, the cathode being sometimes referred to as the "electron-injecting contact layer."

An encapsulation layer 170 is deposited over the contact layer 160 to prevent entry of undesirable components, such as water and oxygen, into the device 100. Such components can have a deleterious effect on the organic layer 130. In one embodiment, the encapsulation layer 170 is a barrier layer or film.

Though not depicted, it is understood that the device 100 may comprise additional layers. For example, there can be a layer (not shown) between the anode 110 and hole transport layer 120 to facilitate positive charge transport and/or bandgap matching of the layers, or to function as a protective layer. Other layers that are known in the art or otherwise may be used. In addition, any of the above-described layers may comprise two or more sub-layers or may form a laminar structure. Alternatively, some or all of anode layer 110 the hole transport layer 120, the electron transport layers 140 and 150, cathode layer 160, and other layers may be treated, especially surface treated, to increase charge carrier transport efficiency or other physical properties of the devices. The choice of materials for each of the component layers is preferably determined by balancing the goals of providing a device with high device efficiency with device operational lifetime considerations, fabrication time and complexity factors and other considerations appreciated by persons skilled in the art. It will be appreciated that determining optimal components, component configurations, and compositional identities would be routine to those of ordinary skill of in the art.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layers 140 and 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In operation, a voltage from an appropriate power supply (not depicted) is applied to the device 100. Current therefore passes across the layers of the device 100. Electrons enter the organic polymer layer, releasing photons. In some OLEDs, called active matrix OLED displays, individual deposits of photoactive organic films may be independently excited by the passage of current, leading to individual pixels of light emission. In some OLEDs, called passive matrix OLED displays, deposits of photoactive organic films may be excited by rows and columns of electrical contact layers.

Devices can be prepared employing a variety of techniques. These include, by way of non-limiting exemplification, vapor deposition techniques and liquid deposition. Devices may also be sub-assembled into separate articles of manufacture that can then be combined to form the device.

Definitions

The use of "a" or "an" are employed to describe elements and components of the invention. This is done merely for convenience and to give a general sense of the invention. This description should be read to include one or at least one and the singular also includes the plural unless it is obvious that it is meant otherwise.

The term "active" when referring to a layer or material is intended to mean a layer or material that exhibits electronic or electro-radiative properties. An active layer material may emit radiation or exhibit a change in concentration of electron-hole pairs when receiving radiation. Thus, the term "active material" refers to a material which electronically facilitates the operation of the device. Examples of active materials include, but are not limited to, materials which conduct, inject, transport, or block a charge, where the charge can be either an electron or a hole. Examples of inactive materials include, but are not limited to, planarization materials, insulating materials, and environmental barrier materials.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "layer" is used interchangeably with the term "film" and refers to a coating covering a desired area. The area can be as large as an entire device or a specific functional area such as the actual visual display, or as small as a single sub-pixel. Films can be formed by any conventional deposition technique, including vapor deposition and liquid deposition. Liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

The term "organic electronic device" is intended to mean a device including one or more semiconductor layers or materials. Organic electronic devices include, but are not limited to: (1) devices that convert electrical energy into radiation (e.g., a light-emitting diode, light emitting diode display, diode laser, or lighting panel), (2) devices that detect signals through electronic processes (e.g., photodetectors photoconductive cells, photoresistors, photoswitches, phototransistors, phototubes, infrared ("IR") detectors, or biosensors), (3) devices that convert radiation into electrical energy (e.g., a photovoltaic device or solar cell), and (4) devices that include one or more electronic components that include one or more organic semiconductor layers (e.g., a transistor or diode). The term device also includes coating materials for memory storage devices, antistatic films, biosensors, electrochromic devices, solid electrolyte capacitors, energy storage devices such as a rechargeable battery, and electromagnetic shielding applications.

The term "substrate" is intended to mean a workpiece that can be either rigid or flexible and may include one or more layers of one or more materials, which can include, but are not limited to, glass, polymer, metal, or ceramic materials, or combinations thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

The term buffer layer is intended to mean an electrically conductive or semiconductive layer and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Buffer materials may be polymers, oligomers, or small molecules and may in the form of solutions, dispersions, suspensions, emulsions, colloidal mixtures or other compositions.

EXAMPLES

The concepts described herein will be further described in the following examples, which do not limit the scope of the invention described in the claims.

Example 1

Example 1 demonstrates the formation of a complex [Y$_2$M-O-]$_n$-CT where CT is a triarylmethane derivative. The complex has the structure:

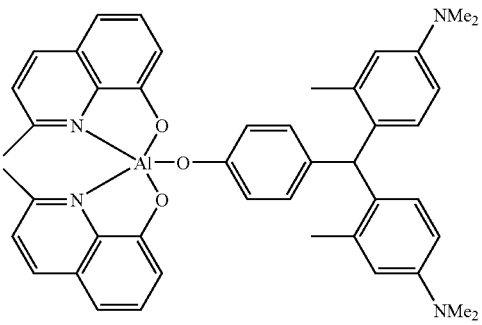

1a) Preparation of Phenolic Triarylmethane Ligand HydroxyMPMP

N,N-dimethyl-m-toluidine (32.6 g) and p-hydroxybenzaldehyde (12.2 g) are mixed together in 30 mL ethanol and 10 mL HCl. The mixture is gently refluxed under nitrogen for 2 days then the resulting mixture is poured into 250 mL water and the pH adjusted to 8 with NaOH. Ethanol is evaporated and the aqueous layer decanted from the solid residue. The solid is washed with distilled water again then the oily solid is triturated with more ethanol until it solidifies. Recrystallization is performed from hot ethanol.

Approximately 28 g of product is recovered by neutralizing (product already solidifies from reaction mixture before addition of water or base). The product is washed well with ethanol and suction dried. Recrystallization is performed from methylene chloride and purified by soxhlet extraction and precipitated with hexanes. The material is not very soluble in methylene chloride. Recovery yields approximately 24 g of white microcrystals. The phenolic triarylmethane ligand, 2-methyl-8-hydroxyquinoline was confirmed by NMR analysis.

1b) Preparation of the Aluminum Complex of Novel Triarylmethane Phenol Prepared in 1a In glove box, 6.4 g of 2-methyl-8-hydroxyquinoline is dissolved into 100 mL toluene with stirring in a 300 mL RB flask. 11 mL of 1.9M triethylaluminum in toluene solution (Aldrich) is added via syringe with rapid stirring. Due to foaming, the addition must be done slowly to prevent overflow. The solution is clear and yellow at this stage. The solution is brought to reflux in a heating mantle and it remains clear yellow. 7.5 g hydroxyMPMP (prepared as described in 1a above) as a solid is added, and the mixture foams again. The mixture is heated and stirred. The solution becomes clear orange-yellow. The mixture is stirred and refluxed with a nitrogen condensor for 1 hr and then cooled. Addition of hexanes produces a whitish precipitate which is collected by filtration and washed with hexanes.

A nicely lemon yellow crystalline material is filtered off from the hexanes/toluene. The material is very soluble in methylene chloride and soluble in hot toluene. The yellow crystals are turquoise luminescent. The crystals are washed with methanol and hexanes and dried to give the sample for NMR. The aluminum complex was confirmed by NMR analysis.

Example 2

Example 2 demonstrates the formation of a complex $[Y_2M\text{-}O\text{-}]_n\text{-}CT$ where CT is a biphenyl, naphthyl, and phenylamine derivative. The complex has the structure:

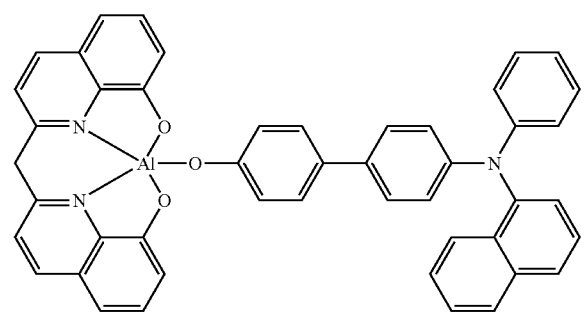

2a) Phenolic Ligand Prep

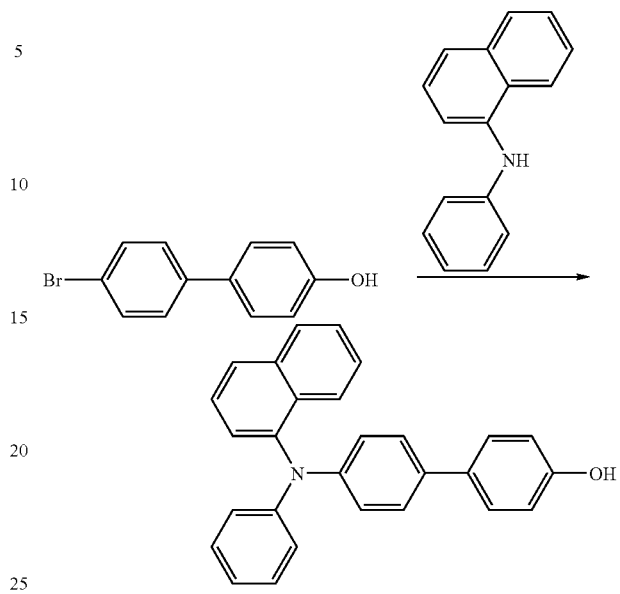

A suspension of $Pd_2(dba)_3$ (1.48 g, 1.61 mmol) and 2-(dicyclohexylphosphino)biphenyl (1.36 g, 3.87 mmol) in THF (30 mL) is stirred for 30 minutes. To this is added 4-bromo-4'-hydroxybiphenyl (8.04 g, 32.3 mmol), N-phenyl-1-napthylamine (14.16 g, 65.6 mmol) and $LiN(SiMe_3)_2$ (11.89 g, 71.0 mmol) with THF (70 mL) and the mixture refluxed for five days after which time it is filtered through silica and washed with brine, drying the organic phase over magnesium sulfate. Upon evaporation a dark red viscous solid is obtained which is purified by chromatography on silica (EtOAc/hex) to afford a pale orange powder (9.2 g, 74%). The product was confirmed by NMR analysis.

2b) Aluminum Complex of Ligand Prepared in (2a)

In a glove box, 1.60 g of quinaldine (2-methyl-8-hydroxyquinoline) is dissolved into 25 mL toluene with stirring in a 300 mL RB flask. 2.75 mL of 1.9M triethylaluminum in toluene solution (Aldrich) is added via syringe with rapid stirring. There is much foaming and the addition must be done slowly to prevent overflow. The solution becomes cloudy and eventually a dense yellow fibrous precipitate forms. The solution is brought to reflux in a heating mantle and it becomes clear yellow. 1.94 g phenol ligand from 2a above is added as a solution in 5 mL toluene, with foaming, and the solution is heated and stirred as a pale orange solution. Reflux is performed for 30 mins.

A pale yellow solid precipitates from the toluene solution on cooling and addition of hexanes leads to additional yellow ppt which may be recovered by filtration. The solid is suction dried to yield 3.5 g of product. The aluminum complex was confirmed by NMR analysis. Melting Point 235° C., Tg: 136° C.

Example 3

Example 3 demonstrates the formation of a complex $[Y_2M\text{-}O\text{-}]_n\text{-}CT$ where CT is a 9-phenylcarbazole derivative. The complex has the structure:

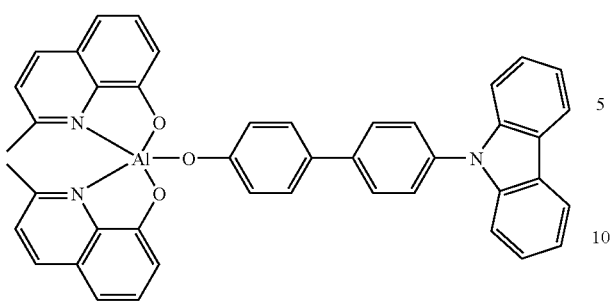

3a) Phenolic Ligand Prep

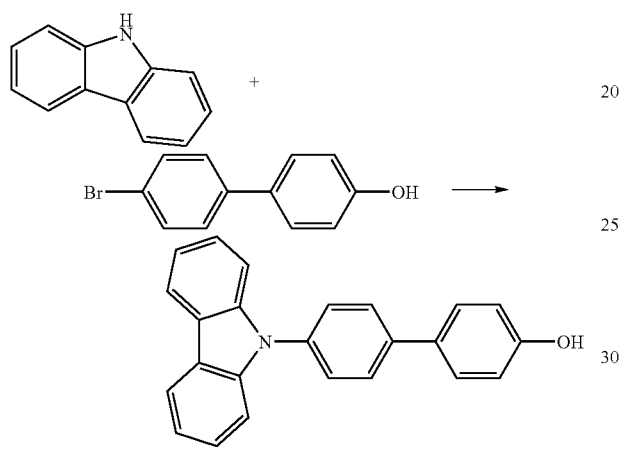

A mixture of 4-bromo-4'-hydroxybiphenyl (5.0 g, 2.01×$10^{-2}$ mol) and carbazole (4.03 g, 2.41×$10^{-2}$ mol) in toluene (20 mL) and dioxane (20 mL) are stirred under nitrogen. To this solution $Pd_2(dba)_3$ (0.350 g, 3.82×$10^{-4}$ mol) and $P(tBu)_3$ (0.077 g, 3.82×$10^{-4}$ mol) are added followed by $LiN(SiMe_3)_2$ (7.4 g, 2.41×$10^{-2}$ mol). The resulting mixture is heated to at 80° C. for 48 hrs. After cooling to room temperature, 1M HCl (10 mL) is added and allowed to stir to 10 minutes. After neutralization with 10% $NaHCO_3$ the phases are separated and the organic phase washed with water (2×100 mL). The organic phase is dried over magnesium sulphate and the solvent is evaporated. Upon addition of hexane a light brown precipitate is isolated, which is further purified by stirring it in $CH_2Cl_2$ (~30 mL) overnight to yield an off-white solid of the desired product (4.2 g, 63%). The product was confirmed by NMR analysis.

3b) Aluminum Complex of Ligand From Part (3a)

In a glove box, 3.20 g of quinaldine (2-methyl-8-hydroxyquinoline) is weighed out and dissolved into 25 mL toluene with stirring in a 300 mL RB flask. 5.5 mL of 1.9M triethylaluminum in toluene solution (Aldrich) is added via syringe with rapid stirring. There is much foaming and addition must be done slowly to prevent overflow. The solution becomes cloudy and eventually a dense yellow fibrous precipitate forms. The solution is brought to reflux in a heating mantle and it becomes clear yellow. 3.4 g 4-(4'-(9-carbazolyl)-phenyl)-phenol prepared in (3a) above as a solid is added, with foaming, and the solution is heated and stirred as a dark clear orange solution. The solution is refluxed for 10 mins at which time a dense cream precipitate forms. The solution is cooled and methanol is added to the slurry which contains a whitish solid. The solid is collected by filtration and suction dried then washed with methanol and hexanes to leave a pearlescent grey-white solid. This solid is blue luminescent as a solid and green luminescent in methylene chloride solution.

The fibrous, off-white solid is collected and suction dried. Recrystallization is performed in a glove box from methylene chloride and toluene by boiling and filtering and evaporating/cooling to precipitate needles of solid. A silvery grey solid is recovered which is soluble in methylene chloride and the aluminum complex was confirmed by NMR analysis.

Example 4

Example 4 demonstrates the formation of a complex $[Y_2M\text{-}O\text{-}]_n\text{-}CT$ where CT is a [4-(N,N-diphenylamino)phenyl]phenyl(4-hydroxybiphenyl)amine derivative. The complex has the structure:

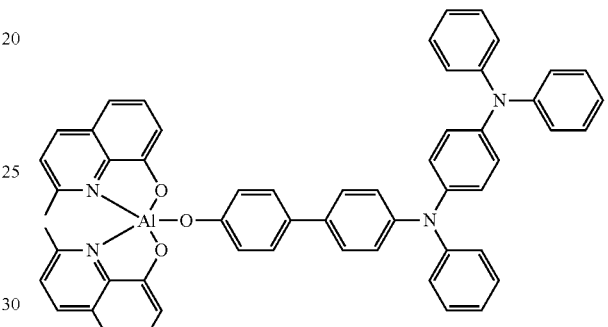

4a) Synthesis of the Phenolic Ligand:

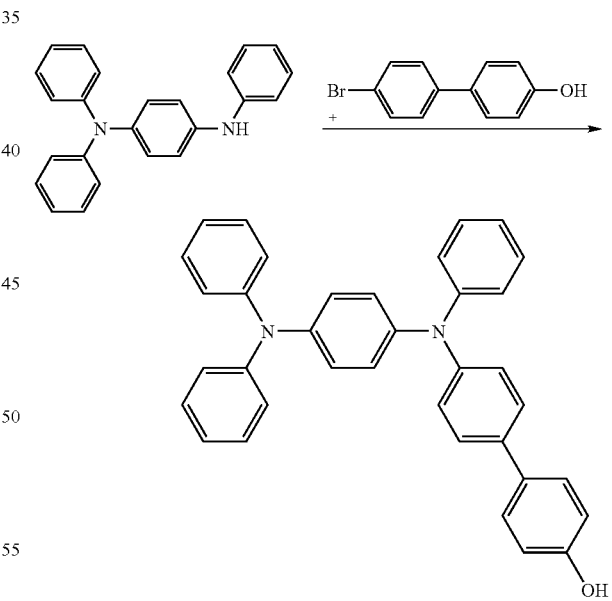

A mixture of 4-bromo-4'-hydroxybiphenyl (13.45 g, 5.3×$10^{-2}$ mol) and [4-(N,N-diphenylamino)phenyl]phenylamine (20 g, 5.9×$10^{-2}$ mol) in toluene (100 mL) and dioxane (100 mL) are stirred under nitrogen. To this solution $Pd_2(dba)_3$ (0.970 g, 1.05×$10^{-3}$ mol) and $P(cyclohexyl)_2$(2-biphenyl) (0.890 g, 2.5×$10^{-3}$ mol) are added followed by $LiN(SiMe_3)_2$ (19.8 g, 1.19×$10^{-2}$ mol). The resulting mixture is heated at 80° C. for 72 hrs. After cooling to room temperature, 1M HCl (50 mL) is added and allowed to stir to 10 minutes. After neutralization with 10% NaHCO$_3$ the phases are separated and the organic phase washed with water (2×200 mL). The organic phase is dried over magnesium sulphate and the solvent is evaporated. Upon addition of hexane a brown solid is obtained which is further purified by chromatography (1:5 EtOAc:hexane) to obtain a light-brown solid in 45% yield (12 g). The product was confirmed by NMR analysis.

4b) Preparation of Aluminum Complex of Ligand Prepared in Part 4a

In a glove box, 1.60 g of quinaldine (2-methyl-8-hydroxyquinoline) was dissolved into 25 mL toluene with stirring in a 300 mL RB flask. 2.75 mL of 1.9M triethylaluminum in toluene solution (Aldrich) was added with a syringe while rapidly stirring. There is much foaming and addition must be done slowly to prevent overflow. The solution becomes cloudy and eventually a dense yellow fibrous ppt forms. The solution is brought to reflux in a heating mantle and it becomes clear yellow. Adding 2.52 g of the phenol prepared in 4a above as a solution in 5 mL toluene and heating and stirring generates a pale orange solution. After refluxing for 30 mins methanol was added and the color lightens slightly. The solution was pumped down under vacuum then methanol was added again. Finally addition of hexanes generates a pale yellow precipitate in ~2 g yield. Solid was dissolved in methylene chloride and the aluminum complex was confirmed by NMR analysis.

Example 5

Example 5 demonstrates the formation of a complex [Y$_2$M-O-]$_n$-CT where CT is a [(N,N'-(diphenyl)(4-hydroxydiphenyl) benzidine derivative. The complex has the structure:

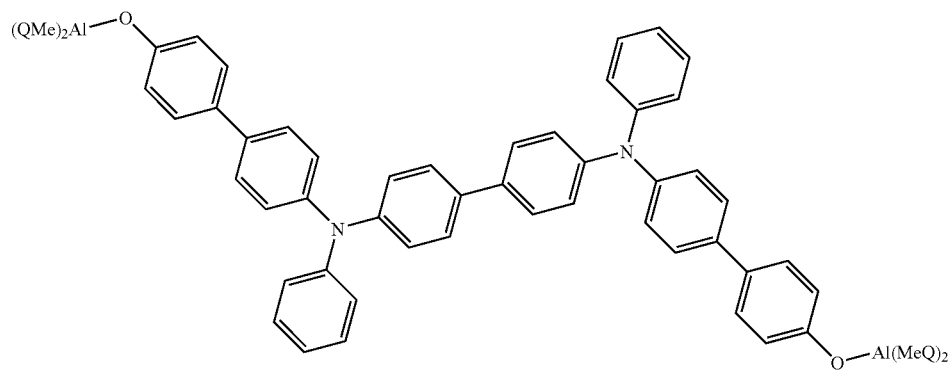

5a) Synthesis of the Phenolic Ligand

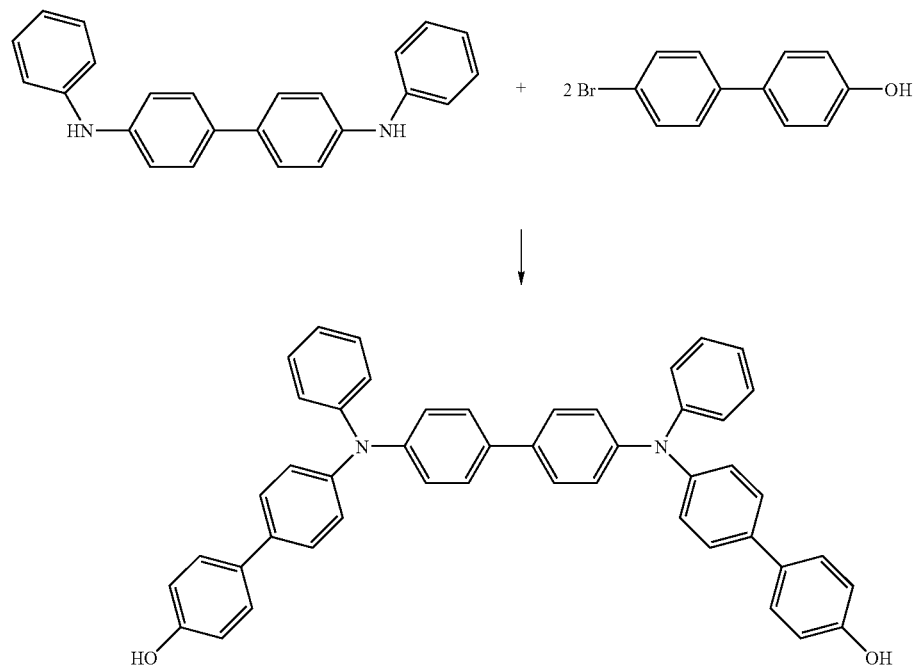

The procedure outlined for example 4 was followed using 4-bromo-4'-hydroxybiphenyl (10.0 g, 4×10⁻² mol) and diphenylbenzidine (5.40 g, 1.6×10⁻² mol), Pd₂(dba)₃ (0.350 g, 3.82×10⁻⁴ mol) and P(tBu)3 (0.077 g, 3.8×10⁻⁴ mol) and LiN(SiMe₃)₂ (29.56 g, 1.77×10⁻¹ mol) in toluene (100 mL) and dioxane (100 mL Upon addition of hexane a brown solid is obtained which is further purified by chromatography (hexane) to obtain a yellow powder in 61% yield (6.6 g).

5b) Preparation of Aluminum Complex of Ligand Prepared in Part 5a

In a glove box, 3.20 g of quinaldine (2-methyl-8-hydroxyquinoline) was dissolved into 25 mL toluene with stirring in a 300 mL RB flask. 5.5 mL of 1.9M triethylaluminum in toluene solution (Aldrich) was added with a syringe and with rapid stirring. There is much foaming and the addition must be done slowly to prevent overflow. The solution becomes cloudy and eventually a dense yellow fibrous ppt forms. Bringing the solution to reflux in heating mantle causes the solution to become clear yellow. Addition of 3.36 g phenol prepared in 5a above as a solution in 5 mL toluene causes the solution to foam again. Refluxing for 30 mins gives a clear pale orange solution. After evaporation, washing the resulting yellow solid with methanol and hexanes yields a dry yellow powder which was confirmed as the aluminum complex by NMR analysis. The solubility of the material is poor in common organic solvents.

Example 6

Example 6 demonstrates the formation of a complex $[Y_2M\text{-}O\text{-}]_n\text{-}CT$ where CT is a [(1,3-di(2-hydroxycarbazole) benzene] derivative. The complex has the structure:

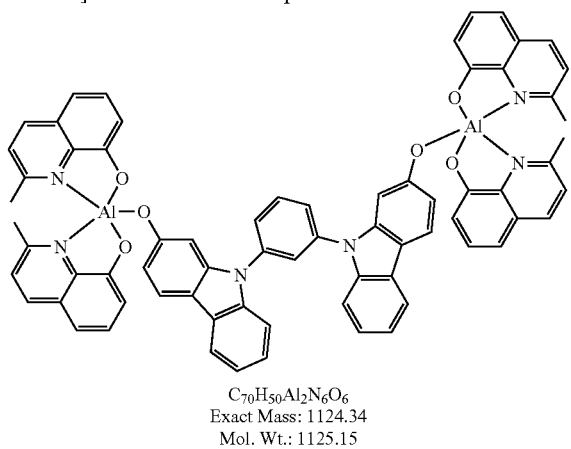

C₇₀H₅₀Al₂N₆O₆
Exact Mass: 1124.34
Mol. Wt.: 1125.15

6a) Synthesis of the Phenolic Ligand

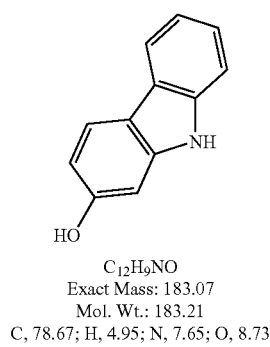

C₁₂H₉NO
Exact Mass: 183.07
Mol. Wt.: 183.21
C, 78.67; H, 4.95; N, 7.65; O, 8.73

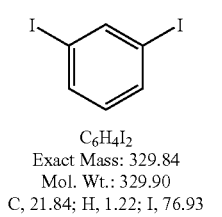

C₆H₄I₂
Exact Mass: 329.84
Mol. Wt.: 329.90
C, 21.84; H, 1.22; I, 76.93

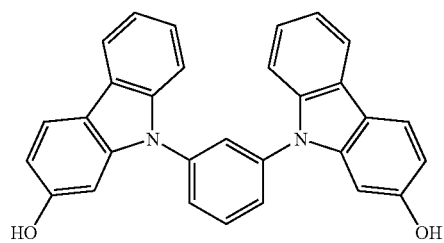

C₃₀H₂₀N₂O₂
Exact Mass: 440.15
Mol. Wt.: 440.49
C, 81.80; H, 4.58; N, 6.36; O, 7.26

The procedure outlined for example 4 was followed using 1,3-diiodobenzene (5.0 g, 1.5×10⁻² mol), 2-hydroxycarbazole (6.11 g, 3.3×10⁻² mol), Pd₂(dba)₃ (0.690 g, 7.58×10⁻⁴ mol) and P(tBu)3 (0.15 g, 7.58×10⁻⁴ mol) and LiN(SiMe₃)₂ (11.16 g, 6.67×10⁻² mol) in toluene (124 mL) and dioxane (125 mL). The product was purified by chromatography (hexane) to obtain a yellow powder in 45% yield (3.0 g). The product was confirmed by NMR analysis.

6b) Preparation of Aluminum Complex of Ligand Prepared in Part 6a

In a glove box, 2.80 g of quinaldine (2-methyl-8-hydroxyquinoline) was dissolved into 25 mL toluene with stirring in a 300 mL RB flask. 4.75 mL of 1.9M triethylaluminum in toluene solution (Aldrich) was added with a syringe with rapid stirring. There is much foaming and the addition must be done slowly to prevent overflow. The solution becomes cloudy and eventually a dense yellow fibrous ppt forms. The solution is brought to reflux in a heating mantle and it becomes clear yellow. 1.9 g diphenol prepared in 6a above is added as a solid and upon heating and stirring the solution becomes very dark clear orange. Reflux for 10 mins at which point it is dark brown. Evaporate to dryness under vacuum and wash with hexanes. Extract into hot methanol and filter. Yellow solid ppts in the filtrate and is collected by filtration and suction dried. The product is extremely soluble in toluene and can be recrystallized from hot methanol as a crystalline yellow solid with green luminescence. The product was confirmed by NMR analysis

Example 7

Example 7 demonstrates the formation of a complex $[Y_2M\text{-}O\text{-}]_n\text{-}CT$ where CT is a [(N,-(1-naphthyl)(phenyl)-N'-(1-naphthyl)(4-hydroxybiphenyl) benzidinederivative. The complex has the structure:

7a) Synthesis of the Phenolic Ligand

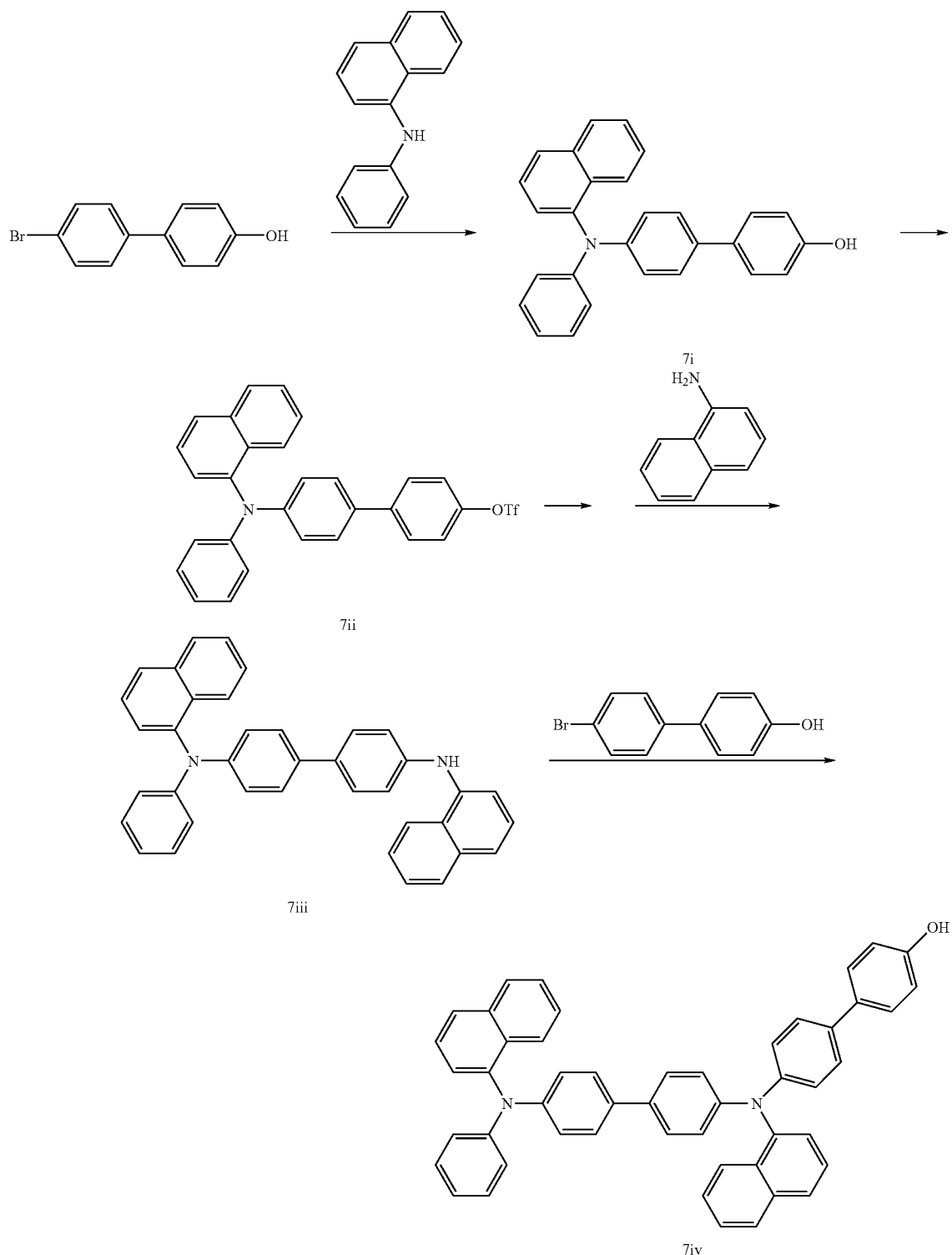

Synthesis of Compound 7i:

A suspension of $Pd_2(dba)_3$ (1.48 g, 1.61 mmol) and 2-(dicyclohexylphosphino)biphenyl (1.36 g, 3.87 mmol) in THF (30 mL) was stirred for 30 minutes. To this was added 4-bromo-4'-hydroxybiphenyl (8.04 g, 32.3 mmol), N-phenyl-1-napthylamine (14.16 g, 65.6 mmol) and $LiN(Si(Me)_3)_2$ (11.89 g, 71.0 mmol) with THF (70 mL) and the mixture refluxed for five days after which time it was filtered through silica and washed with brine, drying the organic phase over magnesium sulfate. Upon evaporation a dark red viscous solid was obtained which was purified by chromatography on silica (EtOAc/hex) to afford a pale orange powder (9.2 g, 74%). Compound 7i was confirmed by NMR analysis.

Synthesis of Compound 7ii:

Trifflic anhydride (8.04 g, 28.5 mmol) was added dropwise to a mixture of 7i (9.20 g, 23.7 mmol) and pyridine (4.88 g, 61.7 mmol) in dichloromethane (140 mL). After 15 minutes stirring the mixture turned from orange to black, four days later the mixture was diluted with dichloromethane and washed with water (3×200 mL) then dried over magnesium sulfate. Upon evaporation of solvent a dark red viscous material was obtained, part of which was purified by extraction into hexanes and the remaining insoluble material by chromatography on silica (hexanes) to give a pale pink powder (total yield: 9.21 g, 75%). Compound 7ii was confirmed by NMR analysis. Synthesis of compound 7iii:

A mixture of 7ii (1.00 g, 1.93 mmol), 1-napthylamine (0.33 g, 2.31 mmol), NaO$^t$Bu (0.26 g, 2.70 mmol), Pd$_2$(dba)$_3$ (0.09 g, 0.096 mmol) and 2-(ditertbutylphosphino)biphenyl (0.029 g, 0.096 mmol) in toluene (20 mL) was refluxed for 24 hours and then filtered through celite and silica. Upon evaporation of the solvent a yellow powder was obtained which was purified by stirring in hexanes to yield a pale yellow powder (0.68 g, 69%). Compound 7iii was confirmed by NMR analysis.

Synthesis of Compound 7iv:

The procedure developed for the synthesis of 7i was employed using Pd$_2$(dba)$_3$ (0.055 g, 0.06 mmol), P(tBu)$_3$ (0.03 g, 0.144 mmol), 4-bromo-4'-hydroxybiphenyl (1.79 g, 7.2 mmol), 7iii (3.06 g, 6.0 mmol) and LiN(SiMe$_3$)$_2$ (2.89 g, 17.3 mmol) in THF (50 mL) to obtain 2.57 g (63%) of desired product 7iv.

7b) Preparation of Aluminum Complex of Ligand 7iv Prepared in Part 7a

In a glove box, 0.80 g of quinaldine (2-methyl-8-hydroxyquinoline) was dissolved into 25 mL toluene with stirring in a 300 mL RB flask. 1.4 mL of 1.9M triethylaluminum in toluene solution (Aldrich) was added with a syringe and with rapid stirring. There is much foaming and addition must be done slowly to prevent overflow. The solution becomes cloudy and eventually a dense yellow fibrous precipitate forms. As the solution is brought to reflux in a heating mantle it becomes clear yellow. 1.7g phenol 7iv prepared in example 7a above was added as a solution in 5 mL toluene and the mixture was heated and stirred to yield a pale orange solution. Reflux for 30 mins and then cooling leads to formation of a pale yellow solid precipitate which was collected by filtration and suction dried. The solid was soluble in methylene chloride and the aluminum complex was confirmed by NMR analysis.

Example 8

Example 8 demonstrates the formation of a complex [Y$_2$M-O-]$_n$-CT where CT is a 9-phenyl-4-hydroxycarbazolyl derivative. The complex has the structure:

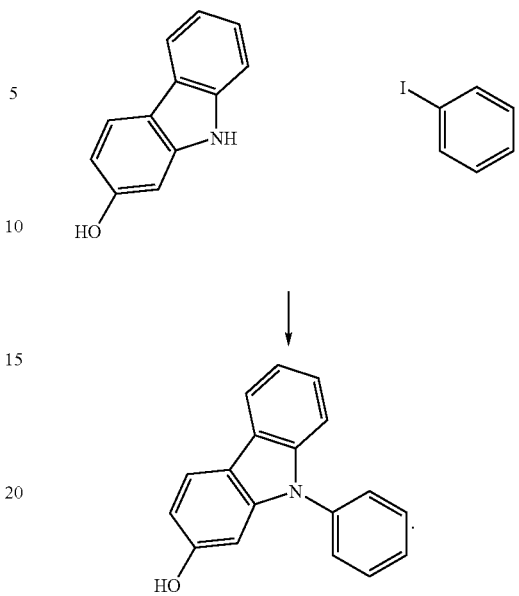

8a) Phenolic Ligand Preparation

The procedure outlined for example 4 was followed using iodobenzene (6.36 g, 3.15×10$^{-2}$ mol), 4-hydroxycarbazole (4.76 g, 2.6×10$^{-2}$ mol), Pd$_2$(dba)$_3$ (0.476 g, 5.2×10$^{-4}$ mol) and P(tBu)3 (0.226 g, 1.12×10$^{-3}$ mol) and LiN(SiMe$_3$)$_2$ (8.70 g, 5.2×10$^{-2}$ mol) in toluene (180 mL) and dioxane (130 mL). The product was purified by silica chromatography (10% ethylacetate in hexane) to obtain a yellow powder in 63% yield (4.25 g).

8b) Preparation of Aluminum Complex of Ligand Prepared in Part 8a

In a glove box, 3.2 g of quinaldine (2-methyl-8-hydroxyquinoline) is dissolved into 25 mL toluene with stirring in a 300 mL RB flask. 5.3 mL of 1.9M triethylaluminum in toluene solution (Aldrich) is added via syringe with rapid stirring. There is much foaming and addition must be done slowly to prevent overflow. The solution becomes cloudy and eventually a dense yellow fibrous ppt forms. Refluxing in a heating mantle produces a clear yellow solution. 2.6 g phenol prepared in 8a above is added as a solution in 5 mL toluene. Heating and stirring produces a pale orange solution. Reflux for 30 mins and then evaporate in vacuum until eventually a creamy ppt appears. Addition of methanol crashes out a microcrystalline solid which is soluble in toluene and methylene chloride. Filter, suction dry and collect ~3 g of product as a pale yellow powder. The aluminum complex was confirmed by NMR analysis.

Example 9

Example 9 demonstrates the formation of a complex [Y$_2$M-O-]$_n$-CT where CT is a 4,4'-(hexafluoroisopropylidine) diphenyl[(N,N'-(4-(N'',N''' diphenyl)aniline)(4-hydroxybiphenyl)derivative. The complex has the structure:

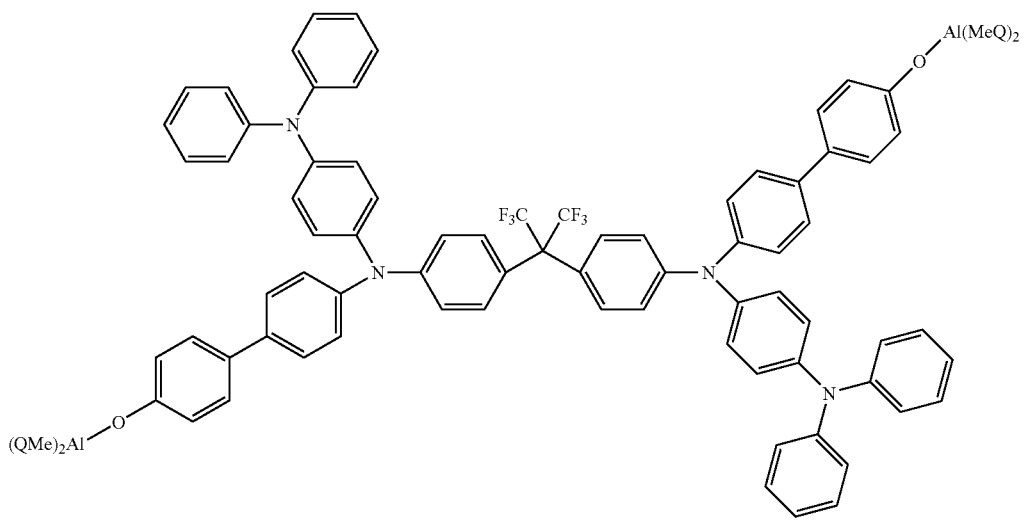
where MeQ represents 2-methyl-8-hydroxyquinoline.
9a) Synthesis of the Phenolic Ligand:
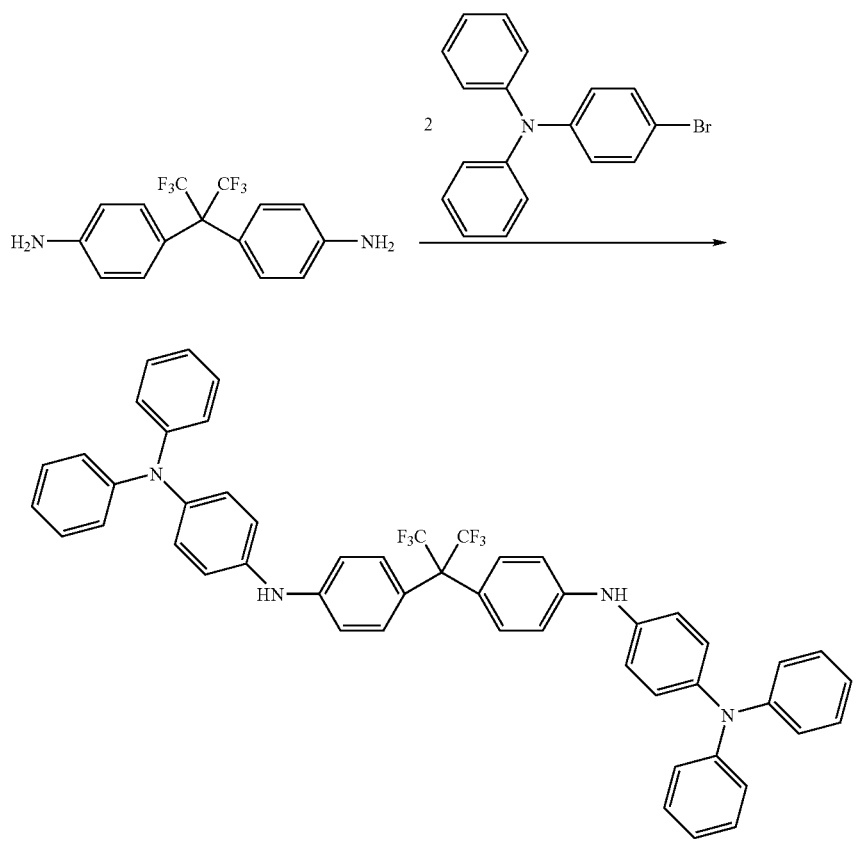
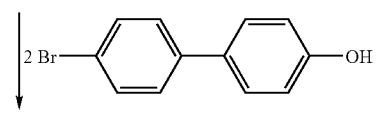

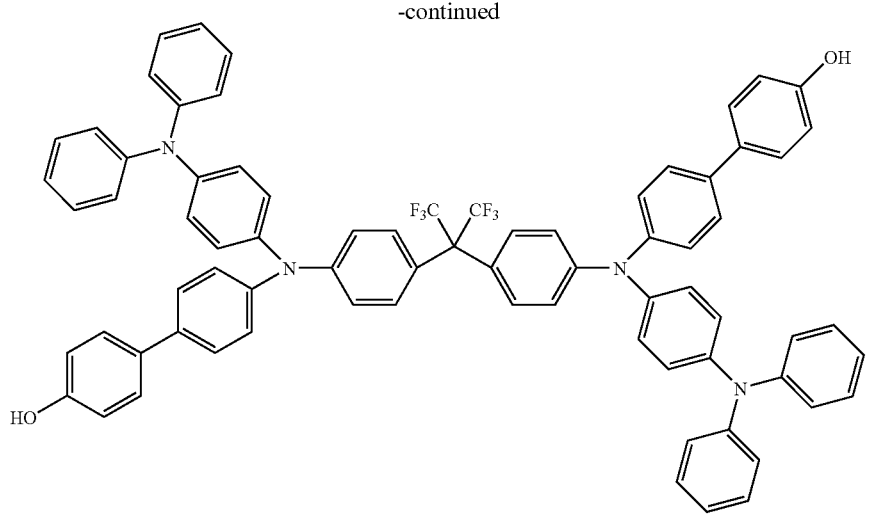

9ii

The procedure outlined for example 4 was followed to obtain compound 9i, using hexafluoroisopropylidene dianiline (10.136 g, 31.26 mmol), $Pd_2(dba)_3$ (0.300 g, 3.28× $10^{-4}$ mol), $P(tBu)_3$ (0.132 g, 6.5×$10^{-4}$ mol) and Na(OtBu) (3.16 g, 32.9 mmol) in toluene (100 mL) for 24 hrs at room temperature. Compound 9i was purified by chromatography (silica/hexane) to obtain 6 g of a white powder (47% yield).

The synthesis of compound 9ii followed the procedure described for example 4 using 4-bromo-4'-hydroxybiphenyl (6.0 g, 2.4×$10^{-2}$ mol) and 9ii (7.9 g, 9.6×$10^{-3}$ mol), $Pd_2(dba)_3$ (0.300 g, 3.28×$10^{-4}$ mol), $P(tBu)_3$ (0.132 g, 6.5×$10^{-4}$ mol) and $LiN(SiMe_3)_2$ (17.73 g, 1.06 mol) in toluene (100 mL) and dioxane (100 mL). The product was purified by washing with acetone/hexane followed by chromatography (silica, THF:hexane—1:10). The product was obtained as a white powder in 51% yield (5.65 g).

9b) Preparation of Aluminum Complex of Ligand Prepared in Part 9a

In a glove box, 3.2 g of quinaldine (2-methyl-8-hydroxyquinoline) is dissolved into 25 mL toluene with stirring in a 300 mL RB flask. 5.3 mL of 1.9M triethylaluminum in toluene solution (Aldrich) is added via syringe with rapid stirring. There is much foaming and addition must be done slowly to prevent overflow. The solution becomes cloudy and eventually a dense yellow fibrous ppt forms. Refluxing in a heating mantle produces a clear yellow solution. 5.8 g bisphenol 9ii prepared in 9a above is added as a solution in 25 mL toluene. Heating and stirring produces a pale orange solution. Reflux for 30 mins and then evaporate in vacuum until eventually a glassy yellow solid appears. Addition of methanol crashes out a yellow solid which is soluble in toluene and methylene chloride. Filter, suction dry and collect ~6.5 g of product as a pale yellow powder. The product is extremely soluble in methylene chloride and toluene but essentially insoluble in methanol. The aluminum complex was confirmed by NMR analysis.

Example 10

Example 10 demonstrates the formation of a complex $[Y_2M-O-]_n$-CT where CT is a 4-hydroxybiphenyl-bis-(4-triphenylamino)-amine derivative. The complex has the structure:

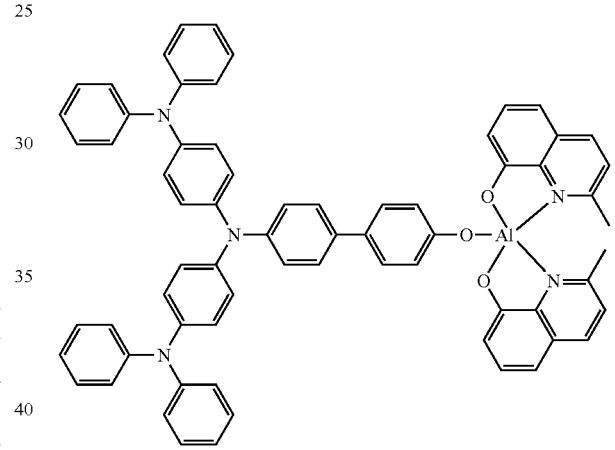

10a) Synthesis of the Phenolic Ligand

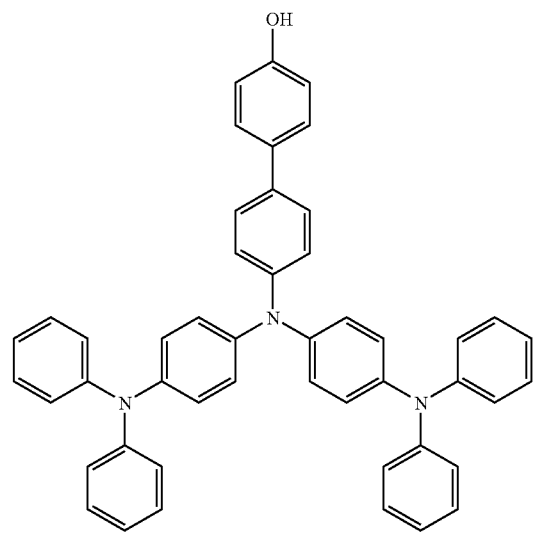

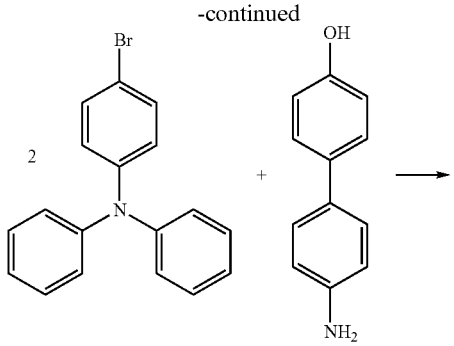

The ligand is synthesized following a procedure similar to that described in example 4 by reaction of 2 mol equivalents of 4-bromophenyl-diphenylamine with 1 mol equivalent of 4-amino-4'-hydroxybiphenyl (Tyger Scientific Inc. 324 Stokes Avenue, Ewing, N.J.,) in the presence of $Pd_2(dba)_3$ (0.01 mol eq) $P(tBu)_3$ (0.022 mol eq) and $LiN(SiMe3)_2$ (3 mol eq) in refluxing toluene for 24 hrs. Compound 10a can be purified by chromatography on silica.

10b) Synthesis of the Aluminum Complex of Ligand Prepared in Part 10a

In a glove box, 3.2 g of quinaldine (2-methyl-8-hydroxyquinoline) is dissolved into 25 mL toluene with stirring in a 300 mL RB flask. 5.3 mL of 1.9M triethylaluminum in toluene solution (Aldrich) is added via syringe with rapid stirring. There should be much foaming and addition is done slowly to prevent overflow. Refluxing in a heating mantle is performed to produce a clear yellow solution. 6.71 g phenol prepared in 10a above is added as a solution in 10 mL toluene. The solution is maintained at reflux for 30 mins and is evaporated in a vacuum, which should generate a creamy ppt. Methanol is added to precipitate a microcrystalline solid, which is soluble in toluene and methylene chloride. Filtering and suction drying will allow collection of the The desired product is a pale yellow powder that can be collected after filtering and suction drying.

Example 11

Example 11 demonstrates the formation of a complex $[Y_2M\text{-}O\text{-}]_n\text{-}CT$ where CT is a 9-phenyl-2-hydroxycarbazolyl derivative. The complex has the structure:

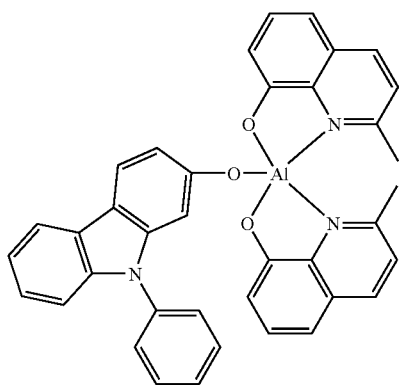

11a) Phenolic Ligand Preparation

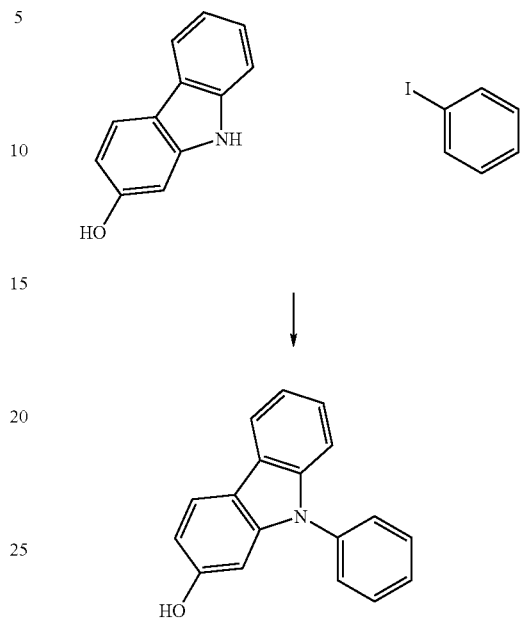

The procedure outlined for example 4 is followed using iodobenzene (6.36 g, $3.15\times10^{-2}$ mol), 2-hydroxycarbazole (4.76 g, $2.6\times10^{-2}$ mol), $Pd_2(dba)_3$ (0.476 g, $5.2\times10^{-4}$ mol) and P(tBu)3 (0.226 g, $1.12\times10^{-3}$ mol) and $LiN(SiMe_3)_2$ (8.70 g, $5.2\times10^{-2}$ mol) in toluene (180 mL) and dioxane (130 mL). The product can be purified by silica chromatography (10% ethylacetate in hexane) to obtain a yellow powder.

11b) Preparation of Aluminum Complex of Ligand Prepared in Part 11a

In a glove box, 3.2 g of quinaldine (2-methyl-8-hydroxyquinoline) is dissolved into 25 mL toluene with stirring in a 300 mL RB flask. 5.3 mL of 1.9M triethylaluminum in toluene solution (Aldrich) is added via syringe with rapid stirring. There should be much foaming and addition is done slowly to prevent overflow. The solution should become cloudy and a dense yellow fibrous ppt should form. Refluxing in a heating mantle is performed to produce a clear yellow solution. 2.6 g phenol prepared in 11a, above, is added as a solution in 5 mL toluene. Heating and stirring produces a pale orange solution. The solution is maintained at reflux for 30 mins and then the solution is evaporated in vacuum until eventually a creamy ppt appears. Methanol is added to precipitate out a microcrystalline solid, which is soluble in toluene and methylene chloride. The solid is collected after filtering followed by suction drying. The solid should appear as a pale yellow powder.

Example 12

Example 12 demonstrates the formation of a complex $[Y_2M\text{-}O\text{-}]_n\text{-}CT$ where CT is a [(4,4'-di(4-hydroxycarbazole) biphenyl] derivative. The complex has the structure:

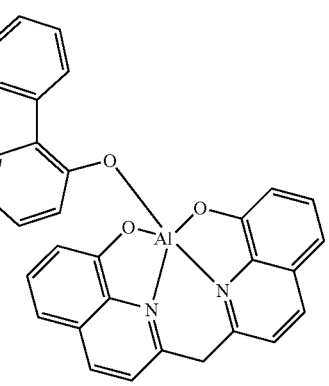

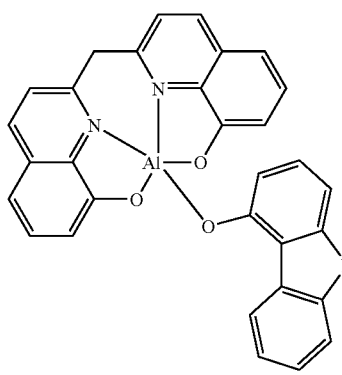

12a) Synthesis of the Phenolic Ligand

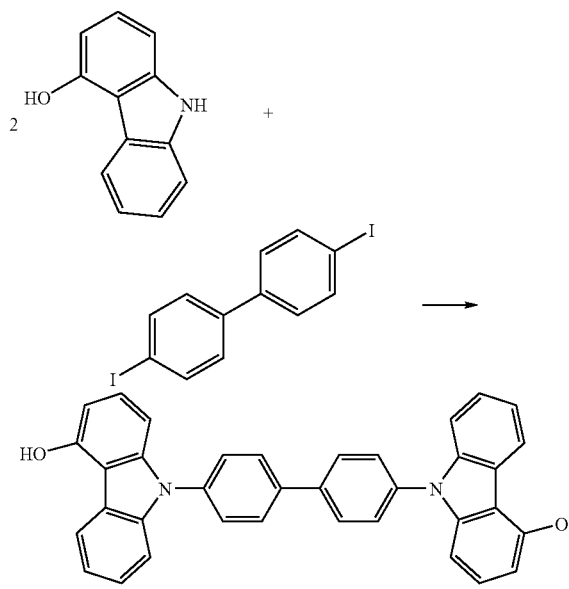

The procedure outlined for example 4 is followed using 4,4'-diiodobiphenyl (1 mol eq), 4-hydroxycarbazole (2 mol eq), Pd$_2$(dba)$_3$ (0.05mol eq) and P(tBu)3 (0.05 mol eq) and LiN(SiMe$_3$)$_2$ (4 mol eq) in toluene and dioxane 1:1. The product can be purified by chromatography on silica (hexane) to remove any singly reacted biphenyl materials.

12b) Preparation of Aluminum Complex of Ligand Prepared in Part 12a

In a glove box, 2 mol eq of quinaldine (2-methyl-8-hydroxyquinoline) is dissolved into toluene with stirring in a RB flask. 1 mol. eq of triethylaluminum in toluene solution (Aldrich) is added with a syringe with rapid stirring. The addition is done slowly to prevent overflow. The solution is brought to reflux in a heating mantle until it becomes clear yellow. 0.5 mol eq of the diphenol prepared in 12a, above, is added as a solid and upon heating and stirring the solution will become clear. The solution is maintained at reflux for 10 mins and is followed by evaporating to dryness under vacuum. The solution is washed with hexanes to isolate the desired product as a solid material. Purification can be achieved by chromatography on silica and/or recrystallization Example 13

Example 13 demonstrates the formation of a complex [Y$_2$M-O-]$_n$-CT where CT is a [(4(diphenylamine)biphenylether) derivative. The complex has the structure:

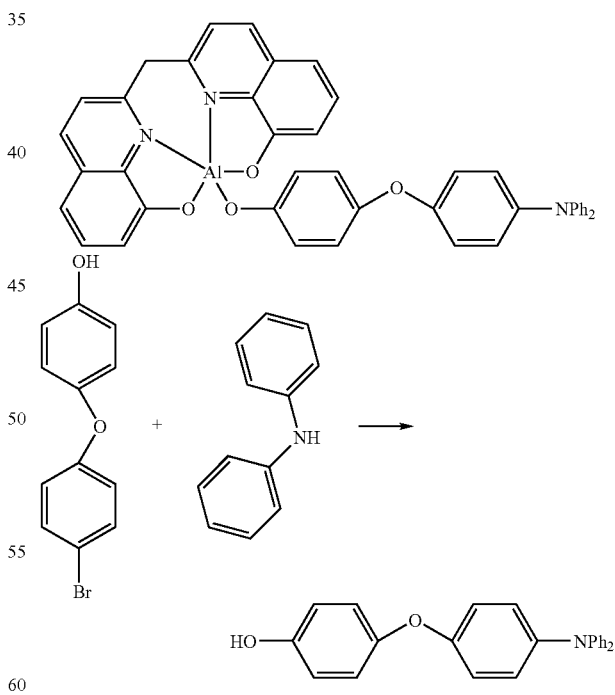

13a) Synthesis of the Phenolic Ligand

The procedure outlined for example 4 is followed using 4-bromo-4-hydroxy-diphenylether (1 mol eq), diphenylamine (1 mol eq), Pd$_2$(dba)$_3$ (0.05 mol eq) and P(tBu)3 (0.05 mol eq) and LiN(SiMe$_3$)$_2$ (2 mol eq) in toluene and dioxane 1:1. The product can be purified by chromatography on silica.

13b) Preparation of Aluminum Complex of Ligand Prepared in Part 13a

In a glove box, 2 mol eq of quinaldine (2-methyl-8-hydroxyquinoline) is dissolved into toluene with stirring in a RB flask. 1 mol. eq of triethylaluminum in toluene solution (Aldrich) is added with a syringe with rapid stirring. The addition is done slowly to prevent overflow. The solution is brought to reflux in a heating mantle until it becomes clear yellow. 1 mol eq of the phenol prepared in 13a, above, is added as a solid and upon heating and stirring the solution should become clear. The solution is maintained at reflux for 10mins and is followed by evaporating to dryness under vacuum. The solution is washed with hexanes to isolate the desired product as a solid material. Purification can be achieved by chromatography on silica and/or recrystallization Example 14

Example 14 demonstrates the formation of a complex [$Y_2$M-O-]$_n$-CT where CT is a [(4(carbazole)biphenylether) derivative. The complex has the structure:

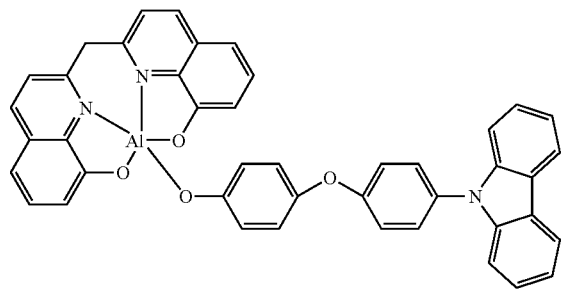

14a) Synthesis of the Phenolic Ligand

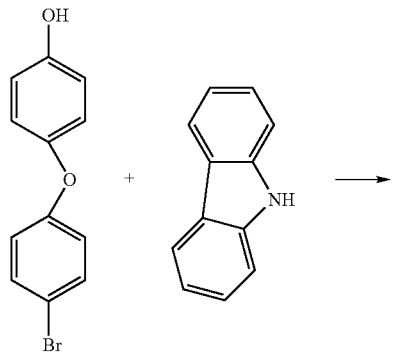

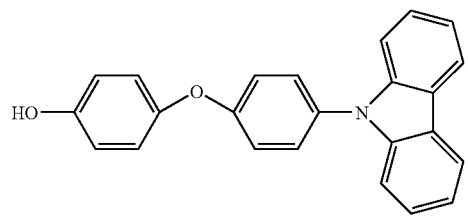

The procedure outlined for example 4 is followed using 4-bromo-4-hydroxy-diphenylether (1 mol eq), carbazole (1 mol eq), Pd$_2$(dba)$_3$ (0.05mol eq) and P(tBu)3 (0.05 mol eq) and LiN(SiMe$_3$)$_2$ (2 mol eq) in toluene and dioxane 1:1. The product can be purified by chromatography on silica.

14b) Preparation of Aluminum Complex of Ligand Prepared in Part 14a

In a glove box, 2 mol eq of quinaldine (2-methyl-8-hydroxyquinoline) is dissolved into toluene with stirring in a RB flask. 1 mol. eq of triethylaluminum in toluene solution (Aldrich) is added with a syringe with rapid stirring. The addition is done slowly to prevent overflow. The solution is brought to reflux in a heating mantle until it becomes clear yellow. 1 mol eq of the phenol prepared in 14a, above, is added as a solid and upon heating and stirring the solution should become clear. The solution is maintained at reflux for 10 mins and is followed by evaporating to dryness under vacuum. The solution is washed with hexanes to isolate the desired product as a solid material. Purification can be achieved by chromatography on silica and/or recrystallization.

Example 15

Example 15 demonstrates the formation of a complex [$Y_2$M-O-]$_n$-CT where CT is a [(3,6-di(N-(4-hydroxycarbazole)dibenzothiophene) derivative. The complex has the structure:

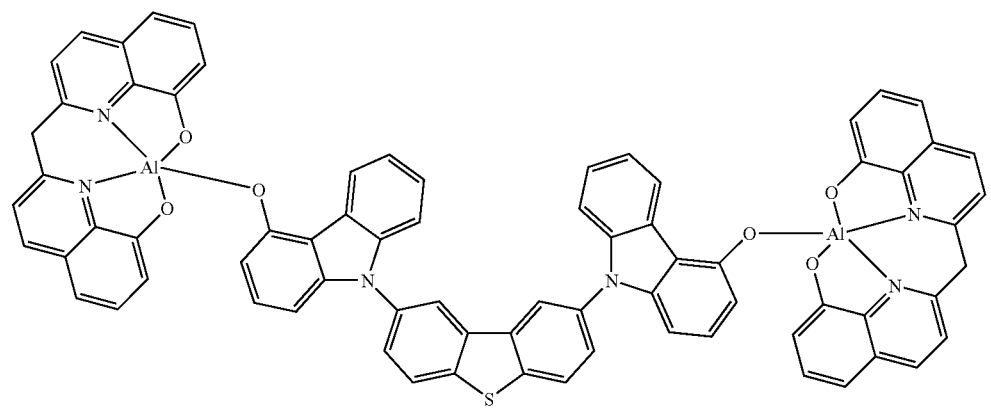

15a) Synthesis of the Phenolic Ligand

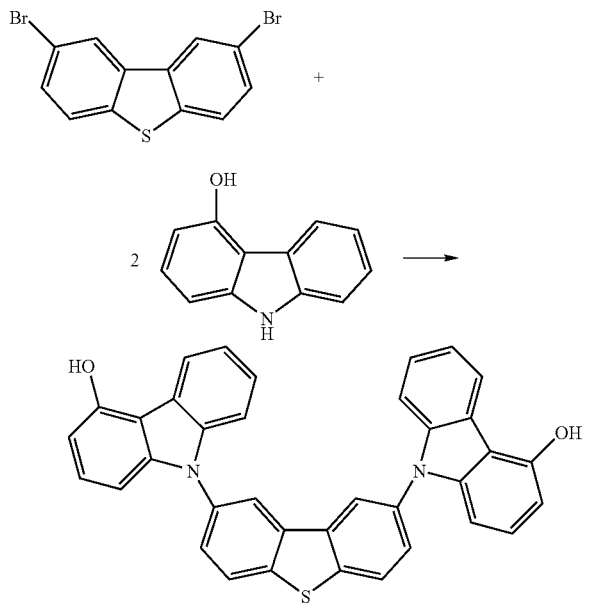

The procedure outlined for example 4 is followed using 3,6-dibromo-dibenzothiophene (1 mol eq), 4-hydroxycarbazole (2 mol eq), $Pd_2(dba)_3$ (0.05 mol eq) and $P(tBu)3$ (0.05 mol eq) and $LiN(SiMe_3)_2$ (4 mol eq) in toluene and dioxane 1:1. The product can be purified by chromatography on silica.

15b) Preparation of Aluminum Complex of Ligand Prepared in Part 15a

In a glove box, 2 mol eq of quinaldine (2-methyl-8-hydroxyquinoline) is dissolved into toluene with stirring in a RB flask. 1 mol. eq of triethylaluminum in toluene solution (Aldrich) is added with a syringe with rapid stirring. The addition is done slowly to prevent overflow. The solution is brought to reflux in a heating mantle until it becomes clear yellow. 0.5 mol eq of the diphenol prepared in 15a, above, is added as a solid and upon heating and stirring the solution should become clear. The solution is maintained at reflux for 10 mins and is followed by evaporating to dryness under vacuum. The solution is washed with hexanes to isolate the desired product as a solid material. Purification can be achieved by chromatography on silica and/or recrystallization.

Example 16

Example 16 demonstrates the formation of a complex $[Y_2M-O-]_n$-CT where CT is a [(1,3-di(4-hydroxycarbazole)benzene] derivative. The complex has the structure:

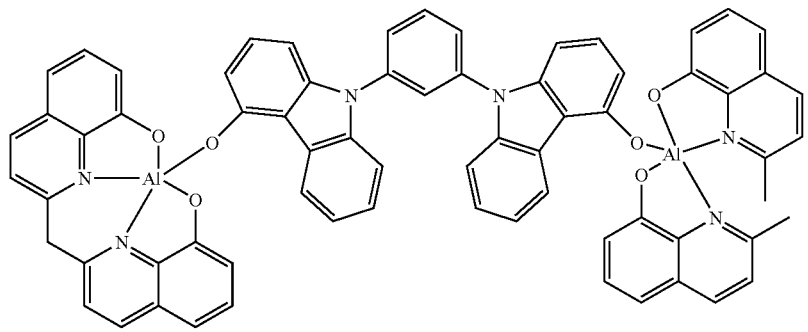

16a) Synthesis of the Phenolic Ligand

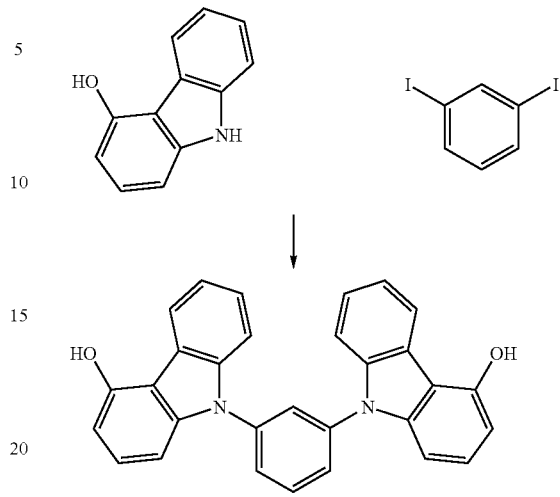

The procedure outlined for example 4 is followed using 1,3-diiodobenzene (5.0 g, $1.5 \times 10^{-2}$ mol), 4-hydroxycarbazole (6.11 g, $3.3 \times 10^{-2}$ mol), $Pd_2(dba)_3$ (0.690 g, $7.58 \times 10^{-4}$ mol) and $P(tBu)3$ (0.15 g, $7.58 \times 10^{-4}$ mol) and $LiN(SiMe_3)_2$ (11.16 g, $6.67 \times 10^{-2}$ mol) in toluene (124 mL) and dioxane (125 mL). The product can be purified by chromatography (hexane) to obtain a yellow powder.

16b) Preparation of Aluminum Complex of Ligand Prepared in Part 16a

In a glove box, 2.80 g of quinaldine (2-methyl-8-hydroxyquinoline) is dissolved into 25 mL toluene with stirring in a 300 mL RB flask. 4.75 mL of 1.9M triethylaluminum in toluene solution (Aldrich) is added with a syringe with rapid stirring. There should be much foaming and the addition is done slowly to prevent overflow. The solution should become cloudy and eventually a dense yellow fibrous ppt should form. The solution is brought to reflux in a heating mantle and should turn clear yellow. 1.9 g diphenol prepared in 16a, above, is added as a solid and upon heating and stirring the solution should become very dark clear orange. The solution is maintained at reflux for 10 mins and should become dark brown. The solution is evaporated to dryness under vacuum and is washed with hexanes. The solution is extracted into hot methanol and filtered. Yellow solid ppts should appear in the filtrate and is collected by filtration and suction dried. The product is extremely soluble in toluene and can be recrystallized from hot methanol as a crystalline yellow solid with green luminescence.

Example 17

Device Fabrication and Characterization Data

OLED devices were fabricated by the thermal evaporation technique. A base vacuum for all of the thin film deposition was applied. Patterned indium tin oxide coated glass substrates from Thin Film Devices, Inc were used. These ITO's are based on Corning 1737 glass coated with 1400 Å ITO coating, with sheet resistance of 30 ohms/square and 80% light transmission. The patterned ITO substrates were then cleaned, rinsed, and then degreased.

The cleaned, patterned ITO substrate was then loaded into the vacuum chamber and further cleaned. After cleaning, multiple layers of thin films were then deposited sequentially onto the substrate by thermal evaporation. Patterned metal electrodes (LiF/Al) were deposited through a mask. The thickness of the films was measured during deposition using a quartz crystal monitor. The completed OLED device was then taken out of the vacuum chamber, encapsulated with a cover glass using epoxy, and characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W.

The material used in device fabrication are listed below:
PEDOT HT: polythiophene with colloid forming fluorinated polymeric acids
NPB: N,N'-Bis(naphthalen-1-yl)-N,N'-bis-(phenyl)benzidine
TDATA: 4,4',4"-Tris-(N,N-diphenyl-amino)-triphenylamine
MTDATA: 4,4',4"-Tris(N-3-methylphenyl-N-phenyl-amino)-triphenylamine Red emitter 1:

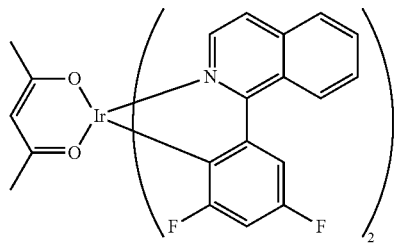

AlQ: Tris-(8-hydroxyquinoline) aluminum
ZrQ: Tetrakis-(8-hydroxyquinoline) zirconium Device Configurations:

Example 17.1

Layers:
ITO substrate
NPB(80 nm)
red emitter 1(3.2 nm) doped in host material of Example 1(40 nm)
AlQ(30 nm)
LiF(1 nm)
Al(100 nm)

Example 17.2

Layers:
ITO substrate
PEDOT HT(44 nm)
NPB(30 nm)
red emitter 1(3.2 nm) doped in host material of Example 2(40 nm)
ZrQ(30 nm)
LiF(1 nm)
Al100 nm)

Example 17.3

Layers:
ITO substrate
PEDOT HT(44 nm)
TDATA(30 nm)
red emitter 1 (3.2 nm) doped in host material of Example 3(40 nm)
ZrQ(30 nm)
LiF(1 nm)
Al(100 nm)

Example 17.4

Layers:
ITO substrate
mTDATA(80 nm)
red emitter 1(3.2 nm) doped in host material of Example 4(40 nm)
ZrQ(30 nm)
LiF(1 nm)
Al(100 nm)

Example 17.5

Layers:
ITO substrate
NPB(80 nm)
red emitter 1(3.2 nm) doped in host material of Example 5(40 nm)
ZrQ(30 nm)
LiF(1 nm)
Al(100 nm)

Example 17.6

Layers:
ITO substrate
PEDOT HT(45 nm)
NPB(30 nm)
red emitter 1(3.2 nm) doped in host material of Example 6(40 nm)
ZrQ(30 nm)
LiF(1 nm)
Al(100 nm)

Example 17.7

Layers:
ITO substrate
PEDOT HT(49 nm)
NPB(30 nm)
red emitter 1(3.2 nm) doped in host material of Example 7(40 nm)
ZrQ(30 nm)

LiF(1 nm)
Al(100 nm)

Example 17.8

Layers:
ITO substrate
PEDOT HT(43 nm)
NPB(30 nm)
red emitter 1(3.2 nm) doped in host material of Example 8(40 nm)
ZrQ(30nm)
LiF(1 nm)
Al(100 nm)

TABLE I

| | Peak efficiency cd/A | Current efficiency at 500 nits, cd/A | Power efficiency at 500 nits, lm/W | Color coordinates, (x, y) |
|---|---|---|---|---|
| Example 17.1 | 4.5 | 3.8 | 1.9 | (0.65, 0.35) |
| Example 17.2 | 10 | 7.8 | 5.5 | (0.65, 0.35) |
| Example 17.3 | 19 | 10 | 4.5 | (0.65, 0.35) |
| Example 17.4 | 2.5 | 2 | 0.8 | (0.65, 0.35) |
| Example 17.5 | 6.5 | 4.3 | 1.5 | (0.66, 0.34) |
| Example 17.6 | 3.6 | 2.1 | 0.7 | (0.65, 0.35) |
| Example 17.7 | 5 | 4.3 | 2 | (0.66, 0.34) |
| Example 17.8 | 11 | 5.4 | 3.4 | (0.65, 0.35) |

Example 18

Solution Processed Device Fabrication and Characterization Data

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with 1400 Å of ITO having a sheet resistance of 30 ohms/square and 80% light transmission. The patterned ITO substrates were cleaned, rinsed, dried, and cleaned again.

A hole injection material, PEDOT HT, was spin-coated over the ITO surface. The cathode leads were wiped clean and the substrates were then baked. After cooling, the substrates were then spin-coated with a 0.4% w/v solution of HT12, the cathode leads were wiped clean, and the substrates were baked in an argon atmosphere. After cooling the substrates were spin-coated with the emissive layer solution from toluene. The cathode contacts were then wiped clean and the substrates were baked in an argon atmosphere. The substrates were masked and placed in a vacuum chamber. A ZrQ layer was deposited by thermal evaporation, followed by a layer of LiF. Masks were then changed in vacuo and a layer of Al was deposited by thermal evaporation. The chamber was vented to argon and the devices were encapsulated using a glass lid, dessicant, and UV curable epoxy. The samples were characterized as described in Example 17.

The materials used in device fabrication are listed below:
PEDOT HT: polythiophene with colloid forming fluorinated polymeric acids
HT-12 available from Dow Chemical
BALq: Bis-(2-methyl-8-quinolinato) 4-phenylphenolate aluminum

H694:

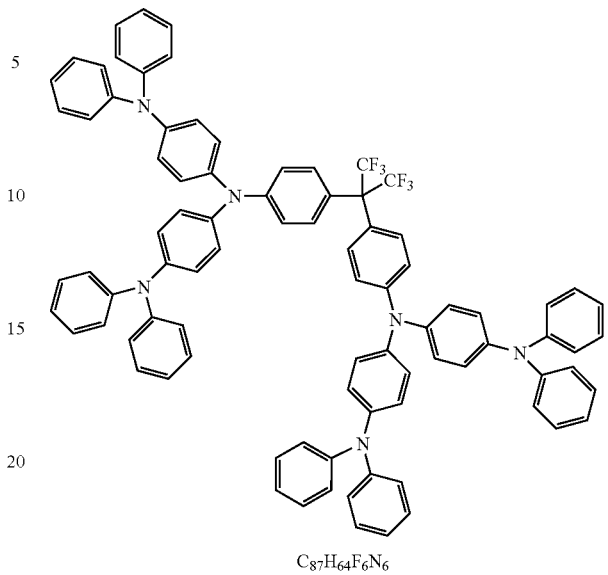

$C_{87}H_{64}F_6N_6$
Exact Mass: 1306.51
Mol. Wt.: 1307.47

Red emitter 1:

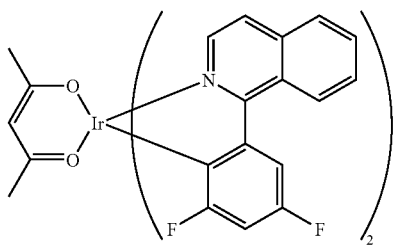

Red emitter 2:

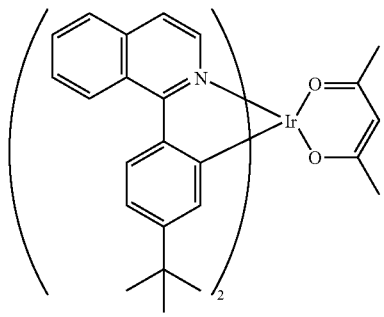

ZrQ: Tetrakis-(8-hydroxyquinoline) zirconium
Device Configurations:

Example 18.1

Layers:
ITO substrate
PEDOT HT(20 nm)
HT12(20 nm), baked at 200° C.
[Host material of Example 4:H694(6:1)]:Red emitter 1(92:8) (50 nm), baked at 90° C.
ZrQ(20 nm)
LiF(0.5 nm)
Al(100 nm)

Example 18.2

Layers:
ITO substrate
PEDOT HT(20 nm)
HT12(20 nm), baked at 195 C.
Host material of Example 4:Red emitter 2(92:8) (53 nm), baked at 105° C.
ZrQ(20 nm)
LiF(0.5 nm)
Al(100 nm)

Example 18.3

Layers:
ITO substrate
PEDOT HT(20 nm)
HT12(20 nm), baked at 195° C.
[Host material of Example 7:H694(4:1)]:Red emitter 2(92:8) (55 nm), baked at 90° C.
ZrQ(20 nm)
LiF(0.5 nm)
Al(100 nm)

Example 18.4

Layers:
ITO substrate
PEDOT HT(20 nm)
HT12(20 nm), baked at 200° C.
Host material of Example 8:Red emitter 1(92:8) (50 nm), baked at 90° C.
ZrQ(20 nm)
LiF(0.5 nm)
Al(100 nm)

Example 18.5

Layers:
ITO substrate
PEDOT HT(20 nm)
HT12(20 nm), baked at 195° C.
Host material of Example 8:Red emitter 2(92:8) (50 nm), baked at 105° C.
ZrQ(20 nm)
LiF(0.5 nm)
Al(100 nm)

Example 18.6

Layers:
ITO substrate
PEDOT HT(20 nm)
HT12(20 nm), baked at 195° C.
Host material of Example 9:Red emitter 2(92:8) (50 nm), baked at 105° C.
ZrQ(20 nm)
LiF(0.5 nm)
Al(100 nm)

TABLE 2

|  | Current efficiency at 500 nits, cd/A | Power efficiency at 500 nits, lm/W | Color coordinates, (x, y) | Lifetime to 50% luminance @ 2000 nits, h |
|---|---|---|---|---|
| Example 18.1 | 3.5 | 1.8 | (0.65, 0.34) | Not tested |
| Example 18.2 | 4.0 | 1.9 | (0.68, 0.31) | Not tested |
| Example 18.3 | 3.4 | 1.7 | (0.68, 0.31) | Not tested |
| Example 18.4 | 4.0 | 2.3 | (0.65, 0.34) | Not tested |
| Example 18.5 | 10.4 | 5.6 | (0.68, 0.31) | 730 |
| Example 18.6 | 3.6 | 1.9 | (0.68, 0.31) | Not tested |

In the foregoing specification, the concepts have been described with reference to specific embodiments. However, one of ordinary skill in the art appreciates that various modifications and changes can be made without departing from the scope of the invention as set forth in the claims below. Accordingly, the specification and FIGURE are to be regarded in an illustrative rather than a restrictive sense, and all such modifications are intended to be included within the scope of invention.

Many aspects and embodiments have been described above and are merely exemplary and not limiting. After reading this specification, skilled artisans appreciate that other aspects and embodiments are possible without departing from the scope of the invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

The invention claimed is:
1. A complex having the formula:

[Y$_2$M-O-]$_n$-CT wherein:
M is a metal in a +2, +3, or +4 oxidation state;
Y is, independently at each occurrence, an hydroxyaryl-N-heterocycle, a bidentate Schiff base ligand, or both Y together form a tetradentate Schiff base ligand;
n is an integer from 1 to 4; and
CT is a charge transport group selected from oxadiazole, phenanthroline, quinoxaline, [(3,6-di(N-(4-hydroxycarbazole)dibenzothiophene), and

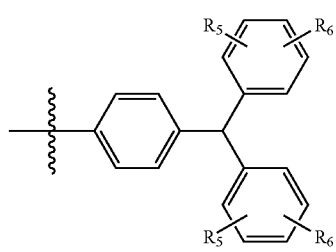

wherein:
R$_5$ is, independently, H or alkyl;
R$_6$ is NR$_7$R$_8$; and $R_7$ and $R_8$ are, independently, alkyl or aryl, or $R_7$ and $R_8$ cooperate to form aryl.

2. The complex of claim 1, wherein Y is 8-hydroxyquinolate.

3. The complex of claim 2, wherein Y is 8-hydroxyquinolate is substituted in the 2 position.

4. The complex of claim 1, wherein Y is 2-(2-hydroxyaryl)pyridine, 2-(2-hydroxyaryl)quinoline, 1-(2-hydroxyaryl)isoquinoline, or 3-(2-hydroxyaryl)isoquinoline.

5. The complex of claim 1, wherein CT is a triarylmethane group, bis[4 (N,N-dimethylamino)-2-methylphenyl](phenyl)methane, 4'-((4-N,N-diphenylamino-phenyl)-phenylamine)-biphenyl, 4'-(bis-(4-N,N-diphenylamino-phenyl)- amine)-biphenyl, [(N,N'-(diphenyl)(4-hydroxybiphenyl) benzidine, oxadiazole, phenanthroline, or quinoxaline.

6. An organic electronic device, comprising:
a photoactive layer; and
the complex of claim 1, wherein the complex is in or adjacent to a photoactive layer.

7. A composition including the complex of claim 1.

8. A ligand for a metal, the ligand having formula I:

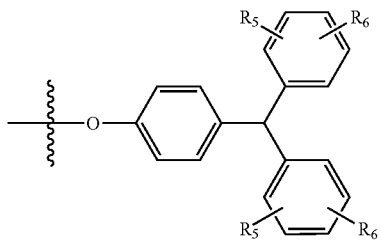

I wherein:
$R_5$ is, independently, H or alkyl;
$R_6$ is $NR_7R_8$; and
$R_7$ and $R_8$ are, independently, alkyl or aryl, or $R_7$ and $R_8$ cooperate to form aryl.

9. The ligand of claim 8, wherein $R_5$ is alkyl at both occurrences and $NR_7R_8$ is $N(Me)_2$.

10. The ligand of claim 8, wherein $R_7$ and $R_8$ are each aryl.

11. An organometallic complex comprising formula VI:

$$[Y]_nMZ \qquad \text{VI}$$

wherein:
n is 1, 2, or 3;
M is a metal in a +2, +3, or +4 oxidation state;
Y is a ligand comprising 8-hydroxyquinoline or alkyl-substituted 8-hydroxyquinoline at each occurrence; and
Z is a ligand according to claim 8.

12. The complex of claim 11, wherein M is Al, Zn, Zr, or Ga.

13. The complex of claim 11, wherein the alkyl-substituted 8-hydroxyquinoline is substituted at the 2 position.

14. The complex of claim 11, wherein the alkyl-substituted 8-hydroxyquinoline is 2-methyl-8-hydroxyquinoline.

15. A composition including the complex of claim 11.

16. An organic electronic device having an active layer including the complex of claim 11.

17. An article useful in the manufacture of an organic electronic device, comprising the complex of claim 11.

18. An organometallic complex having at least one charge transporting ligand, wherein the charge transporting ligand is a triarylmethane group, a triarylamine group, bis[4 (N,N-dimethylamino)-2-methylphenyl](phenyl)methane, 4'-((4-N,N-diphenylamino-phenyl)-phenylamine)-biphenyl, 4'-(bis-(4-N,N-diphenylamino-phenyl)- amine)-biphenyl, [(N,N'-(diphenyl)(4-hydroxybiphenyl) or benzidine.

* * * * *

UNITED STATES PATENT AND TRADEMARK OFFICE
CERTIFICATE OF CORRECTION

PATENT NO. : 8,362,463 B2  Page 1 of 1
APPLICATION NO. : 11/721746
DATED : January 29, 2013
INVENTOR(S) : Radu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1532 days.

Signed and Sealed this
First Day of September, 2015

Michelle K. Lee
*Director of the United States Patent and Trademark Office*